US008481052B2

(12) United States Patent
Choi et al.

(10) Patent No.: US 8,481,052 B2
(45) Date of Patent: Jul. 9, 2013

(54) **AVIRULENT *SALMONELLA GALLINARUM* VARIANTS AND PHARMACEUTICAL COMPOSITION USING THE SAME**

(75) Inventors: Hyang Choi, Anyang-si (KR); Soo An Shin, Seoul (KR); Si Yong Yang, Incheon (KR); Young Wook Cho, Seoul (KR)

(73) Assignee: CJ Cheiljedang Corporation, Seoul (KR)

( * ) Notice: Subject to any disclaimer, the term of this patent is extended or adjusted under 35 U.S.C. 154(b) by 0 days.

(21) Appl. No.: 13/274,854

(22) Filed: Oct. 17, 2011

(65) Prior Publication Data

US 2012/0294892 A1 Nov. 22, 2012

Related U.S. Application Data

(60) Provisional application No. 61/487,137, filed on May 17, 2011.

(51) Int. Cl.
*A61K 39/112* (2006.01)
*C12N 1/20* (2006.01)

(52) U.S. Cl.
USPC ................... 424/235.1; 424/258.1; 435/252.3

(58) Field of Classification Search
None
See application file for complete search history.

(56) References Cited

U.S. PATENT DOCUMENTS

| 6,923,957 | B2 | 8/2005 | Lowery et al. | |
|---|---|---|---|---|
| 7,211,264 | B2 | 5/2007 | Feldman et al. | |
| 7,700,104 | B2 * | 4/2010 | Hensel et al. | 424/184.1 |
| 7,842,290 | B2 * | 11/2010 | Holden | 424/93.2 |
| 7,887,816 | B2 * | 2/2011 | Feldman et al. | 424/258.1 |
| 7,955,600 | B2 * | 6/2011 | Hensel et al. | 424/184.1 |

OTHER PUBLICATIONS

Abrahams, G.L. and Hensel, M., "Manipulating cellular transport and immune responses: dynamic interactions between intracellular *Salmonella enterica* and its host cells,"*Cell. Microbiol.* 8(5):728-37, Blackwell Publishing Ltd., United Kingdom (2006).

Brumme, S., et al., "Impact of *Salmonella* Typhimurium DT104 virulence factors *invC* and *sseD* on the onset, clinical course, colonization patterns and immune response of porcine salmonellosis," *Vet. Microbiol. 124*:274-85, Elsevier B.V., Netherlands (2007).

Desin, T.S., et al., "*Salmonella enterica* Serovar Enteritidis Pathogenicity Island 1 Is Not Essential for but Facilitates Rapid Systematic Spread in Chickens," *Infect. Immun.* 77(7):2866-75, American Society for Microbiology, United States (2009)

Edwards, R., et al., "A role for *Salmonella* fimbriae in intraperitoneal infections," *Proc. Natl. Acad Sci.* 97:1258-1262, National Academy of Sciences, United States (2000).

Edwards, R.A., et al., "Comparative genomics of closely related salmonellae," *Trends Microbiol. 10*(2):94-99, Elsevier Science Ltd., United Kingdom (2001).

Gulig, P.A., et al., "Molecular analysis of *spv* virulence genes of the *Salmonella* virulence plasmids," *Mol. Microbiol.* 7(6):825-30, Blackwell Scientific, United Kingdom (1993).

Hapfelmeier, S., et al., "The *Salmonella* Pathogenicity Island (SPI)-2 and SPI-1 Type III Secretion Systems Allow *Salmonella* Serovar *typhimurium* to Trigger Colitis via MyD88-Dependent and MyD88-Independent Mechanisms," *J. Immunol. 174*:1675-85, The American Association of Immunologists, Inc., United States (2005).

Kimbrough, T.G. and Miller, S.I., "Assembly of the type III secretion needle complex of *Salmonella typhimurium*," *Microbes Infect.* 4:75-82, Elsevier SAS, France (2002).

Lostroh, C.P. and Lee, C.A., "The *Salmonella* pathogenicity island-1 type III secretion system," *Microbes Infect. 3*:1281-91, Elsevier SAS, France (2001).

Schlumberger, M.C. and Hardt, W-D., "*Salmonella* type III secretion effectors: pulling the host cell's strings," *Curr. Opin. Microbiol.* 9:46-54, Current Biology, United Kingdom (2006).

Waterman, S.R. and Holden, D.W., "Functions and effectors of the *Salmonella* pathogenicity island 2 type III secretion system," *Cell. Microbiol.* 5(8):501-11, Blackwell Publishing Ltd., United Kingdom (2003).

* cited by examiner

*Primary Examiner* — Padma V Baskar
(74) *Attorney, Agent, or Firm* — Sterne, Kessler, Goldstein & Fox P.L.L.C.

(57) ABSTRACT

The present invention relates to avirulent *Salmonella gallinarum* variants by inactivating virulence gene clusters of *Salmonella gallinarum* (SG), a main pathogen of avian salmonellosis, and various uses thereof notably in the production of *Salmonella*-specific lytic bacteriophages, pharmaceutical compositions and feed additives.

7 Claims, 2 Drawing Sheets

AVIRULENT *SALMONELLA GALLINARUM* VARIANTS AND PHARMACEUTICAL COMPOSITION USING THE SAME

REFERENCE TO A SEQUENCE LISTING SUBMITTED ELECTRONICALLY VIA EFS-WEB

The content of the electronically submitted sequence listing, file name: sequencelisting_ascii.txt; size: 95,663 bytes; and date of creation: Oct. 14, 2011, filed herewith, is incorporated herein by reference in its entirety.

BACKGROUND OF THE INVENTION

1. Field of the Invention

The present invention provides avirulent *Salmonella* variants and various uses thereof, particularly in the production of *Salmonella*-specific lytic bacteriophages, pharmaceutical compositions, and feed additives.

2. Description of the Related Art

Currently over 2,000 *Salmonella* strains are generally classified into host-specific serotypes, and non-host-specific serotypes pathogenic for both animals and humans. Representative among fowl-adapted pathogens are *Salmonella gallinarum* (SG) and *Salmonella pullorum* (SP) which are known to cause fowl typhoid and pullorum disease, respectively. These *Salmonella*-caused fowl diseases occur at low frequency in advanced countries, but have inflicted tremendous economic damage on the poultry farming in developing countries.

*Salmonella gallinarum* strains have serologically the same somatic antigen (O-antigen) structures and are classified as being non-motile because they have no flagella. When entering into a host animal via contaminated feed or a contaminated environment, *Salmonella* pass through the gastrointestinal tract, and invade intestinal epithelial cells by interaction with Peyer's patch M (microfold) cells and penetrate into the intestinal membrane. *Salmonella* are transported by the M cells to macrophages in adjacent intestinal membranes, and then *Salmonella* infection develops into a systemic disease.

The type III secretion system (TTSS) is a protein appendage found in Gram-negative bacteria, which consists of a needle-like protein complex structure through which virulence effector proteins pass from the bacterial cytoplasm directly into the host cytoplasm (Mota L J et al., Ann Med. (2005); 37(4):234-249). The type III secretion system is essential for the delivery of the pathogenicity of *Salmonella* (Schlumberger M C et al., Curr Opin Microbiol. (2006); 9(1):46-54). Wild-type *Salmonella* take advantage of TTSS when adhering to and invading host cells, and then survives during the phagocytosis of macrophages and circulates throughout the body via the bloodstream, causing a systemic infection. Hence, *Salmonella* infection cannot proceed without the normal operation of TTSS. *Salmonella* pathogenicity island-1 (hereinafter referred to as "SPI-1") is a discrete region of the *Salmonella* chromosome encoding the type III secretion system and virulent effector proteins which are necessary for invasion into intestinal epithelial cells in the early stage of infection (Kimbrough T G et al., Microbes Infect, (2002); 4(1):75-82). *Salmonella* pathogenicity island-2 (hereinafter referred to as "SPI-2") is also a discrete region of the *Salmonella* chromosome encoding the type III secretion system and effector proteins which involved in survival and proliferation during phagocytosis by macrophages in intestinal immune organs or immune organs such as the spleen and the liver after translocation across epithelial cells (Waterman S R et al., Cell Microbiol, (2003); 5(8):501~511, Abrahams G L, Cell Microbiol, (2006); 8(5):728-737). Genes within SPI-1 and SPI-2 and their functions are summarized in Table 1, below.

TABLE 1

| | Gene | Characteristics |
|---|---|---|
| SPI-1 | avrA | putative inner membrane protein |
| | sprB | transcriptional regulator |
| | hilC | bacterial regulatory helix-turn-helix proteins, araC family |
| | orgA | putative flagellar biosynthesis/type III secretory pathway protein |
| | prgK | cell invasion protein; lipoprotein, may link inner and outer membranes |
| | prgJIH | cell invasion protein |
| | hilD | regulatory helix-turn-helix proteins, araC family |
| | hilA | invasion genes transcription activator |
| | iagB | cell invasion protein |
| | sptP | protein tyrosine phosphate |
| | sicP | chaperone, related to virulence |
| | iacP | putative acyl carrier protein |
| | sipADCB | cell invasion protein |
| | sicA | surface presentation of antigens; secretory proteins |
| | spaSRQPO | surface presentation of antigens; secretory proteins |
| | invJICB | surface presentation of antigens; secretory proteins |
| | invAEGFH | invasion protein |
| SPI-2 | ssaUTSRQPONVMLKJIHG | Secretion system apparatus |
| | sseGF | Secretion system effector |
| | sscB | Secretion system chaperone |
| | sseEDC | Secretion system effector |
| | sscA | Secretion system chaperone |
| | sseBA | Secretion system effector |
| | ssaE | Secretion system effector |
| | ssaDCB | Secretion system apparatus |
| | ssrA | Secretion system regulator:Sensor component |
| | ssrB | Secretion system regulator: transcriptional activator, homologous with degU/uvrY/bvgA |

In addition to these type III secretion systems, fimbriae gene (faeHI) (Edwards R A et al., PNAS (2000); 97(3):1258-1262) and the virulent factor (spvRABCD operon) present in virulent plasmids of *Salmonella* are implicated in the virulence of *Salmonella* (Gulig P A et al., Mol Microbiol (1993); 7(6):825-830).

*Salmonella*-caused fowl diseases are difficult to control because they are transmitted in various ways including egg transmission, and feed or environmental infection, and show high recurrence rates even after post-infectious treatment with antibiotics. Therefore, it is importance of preventing the onset of disease by using a vaccine as well as sanitizing breeding farms and feed. In the poultry industry, a lot of effort has been poured into the use of live vaccines (attenuated *Salmonella gallinarum* strains—SG9S, SG9R) and dead vaccines (gel vaccines, oil vaccines, etc.) to prevent the onset of fowl typhoid. However, the effects of the vaccine vary with the concentration of the vaccine used, the condition of the fowl vaccinated, and the environment of chicken houses. And, the efficacy of these vaccines is reported to be significantly lower than that of the vaccines for other diseases. Treatment with antibiotics, although reducing the lesion, converts infected fowls into chronic carriers (See: Incidence and Prevention of Hen Salmonellosis, the National Veterinary Research & Quarantine Service, Korea).

Therefore, new *Salmonella*-controlling approaches that are better than conventional vaccines or antibiotics are being demanded. Many scientists have recently paid attention to bacteriophages, which infect and lyse bacteria specifically and are safe to humans, as a potent alternative to antibiotics. There are many reports concerning the use of bacteriophages being used in the prevention or therapy of *Salmonella* diseases (Atterbury R J et al., Appl Environ Microbiol, (2007); 73(14):4543-4549) and as disinfectants or detergents to prevent the putrefaction of foods (PCT 1998-08944, PCT 1995-31562, EP 1990-202169, PCT 1990-03122), and concerning phage display techniques for diagnosis (Ripp S et al., J Appl Microbiol, (2006); 100(3):488-499), *Salmonella* vaccines prepared by deleting or modifying one or two genes within SPI-2 gene cluster have recently been disclosed (U.S. Pat. No. 6,923,957, U.S. Pat. No. 7,211,264, U.S. Pat. No. 7,887,816).

For industrial use, bacteriophages are produced by separating the phage progenies from the host cells lysed during the proliferation of bacteriphages which have been inoculated into the host cells cultured on a mass scale. As for bacteriophages specific for pathogenic bacteria, however, their lysates may contain the pathogenic host cells being not removed, and/or virulent materials such as pathogenic proteins of the host. This likelihood acts as a great risk factor to the safety of bacteriophages produced on the basis of pathogenic host cells.

Many bacteria have lysogenic phages on their chromosomes; however, most of the phages are cryptic and cannot produce progeny because of the accumulation of many mutations as ancestral remnants. Lysogenic phages, although inactive, may help the survival capacity of *Salmonella* upon host infection because they contain the genes necessary for lytic and lysogenic growth and some of the genes encode pathogenic factors. However, these genes are likely to undergo homologous recombination with the viral genome of other similar phages which newly infect animals, thus producing genetically modified phages. As for the typical *Salmonella typhimurium*, it has fels-1, fels-2, gifsy-1, and gifsy-2 prophages and two cryptic phages. In contrast, *Salmonella gallinarum* could be used as a phage-producing host since *Salmonella gallinarum* have neither prophages nor cryptic phages, and then are not genetically modified by recombination. (Edwards R A et al, Trends Microbiol, (2002); 10(2):94-99).

For the purpose of minimizing toxic remnants during progeny production and phage's opportunity for mutation, the present inventors designed the idea that the virulence gene clusters of *Salmonella gallinarum* could be inactivated for producing bacteriophages. There have no precedent cases wherein avirulent bacteria, which had been converted from virulent bacteria by inactivating a virulence gene cluster, were used as a bacteriophage host cell.

In addition to the production of bacteriophages, the *Salmonella* deprived of virulence by inactivating virulence gene clusters are themselves used for developing attenuated live vaccines for controlling *Salmonella* or applied to the bioindustry, guaranteeing significant added values.

In the present invention, avirulent *Salmonella gallinarum* variants obtained by inactivating at least one of the main *Salmonella* virulence gene clusters (SPI-1, SPI-2, spvRABCD and faeHI operons) are used as a bacteriophage-producing host cell and applied to various uses.

SUMMARY OF THE INVENTION

With the aim of solving the problems with the recombinational modification of progeny phages and the toxic bacterial remnants in the course of bacteriophage production on the basis of the above-described facts, the present inventors developed avirulent *Salmonella gallinarum* variants as a host cell for bacteriophage-producing by inactivating at least one of the four main *Salmonella gallinarum* gene clusters (SPI-1, SPI-2, spvRABCD and faeHI operons). In addition, the present inventors primarily confirmed reduced virulence by measuring the efficiency of the invasion of *Salmonella gallinarum* into avian epithelial cells, and reconfirmed by measuring the mortality of hens infected with avirulent *Salmonella gallinarum* variants. On the other hand, the present inventors approve the use of bacteriophage-producing host, the use of the pharmaceutical compositions and feed additives for the prevention or treatment of avian salmonellosis through comparison of the productivity of bacteriophages between wild-type and the avirulent *Salmonella gallinarum* variants.

It is therefore a primary object of the present invention to provide a *Salmonella gallinarum* variant in which the SPI-2 gene cluster is inactivated, a *Salmonella gallinarum* variant in which both SPI-1 and SPI-2 gene clusters are inactivated, and an avirulent *Salmonella gallinarum* variant in which at least one of the four main virulence gene clusters (SPI-1, SPI-2, spvRABCD, and faeHI operon) has been inactivated.

It is another object of the present invention to provide the use of the avirulent *Salmonella gallinarum* variant in the production of *Salmonella*-specific bacteriophages or a method for producing phages using the avirulent *Salmonella gallinarum* variant. The avirulent *Salmonella gallinarum* variants according to the present invention can be used for the mass-production of *Salmonella*-specific lytic bacteriophages free of remnant toxicity and applied to the development of a novel concept of antibiotic substitutes which have high industrial utility value and guarantee significant added value.

It is a further object of the present invention to provide a pharmaceutical composition comprising avirulent *Salmonella gallinarum* variants as an active ingredient, preferably a live vaccine and a feed additive. The SPI-1 gene cluster encodes type III secretion system proteins which remain on cell surfaces, acting as an antigen while the SPI-2 gene cluster encodes proteins which are involved in survival in the phagosomes after passage across epithelial cells. Hence, the inactivation of the SPI-2 gene cluster alone, with SPI-1 gene cluster remaining intact, leaves the antigen necessary for the production of an antibody inducing an immune response, but does not allow the bacteria to survive during phagocytosis, which does not result in a systemic disease. Thus, the SPI-2 gene cluster-inactivated *Salmonella gallinarum* variant might be used as a live vaccine.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
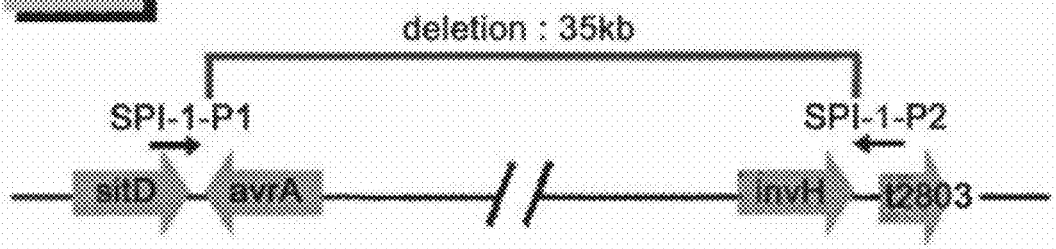
FIG. 1 is a schematic diagram showing virulence genes of avian *Salmonella* (*Salmonella* pathogenicity island-1, *Salmonella* pathogenicity island-2, spvRABCD, faeHI) and sites corresponding to primers for inactivating the virulence genes.
Figure 1:
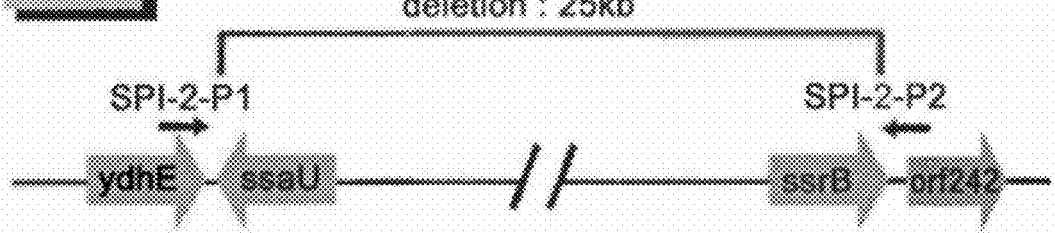
Figure 1:
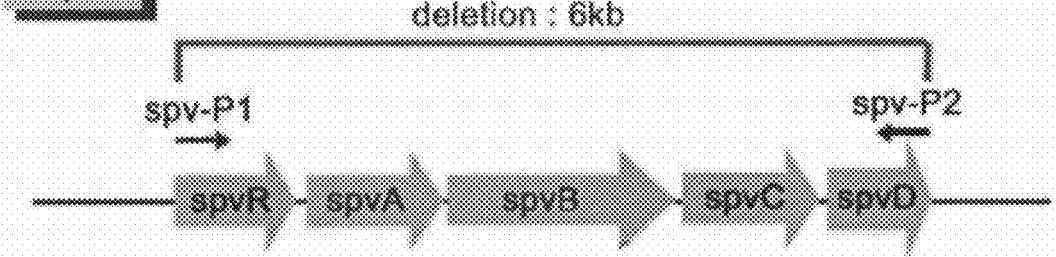
Figure 1:
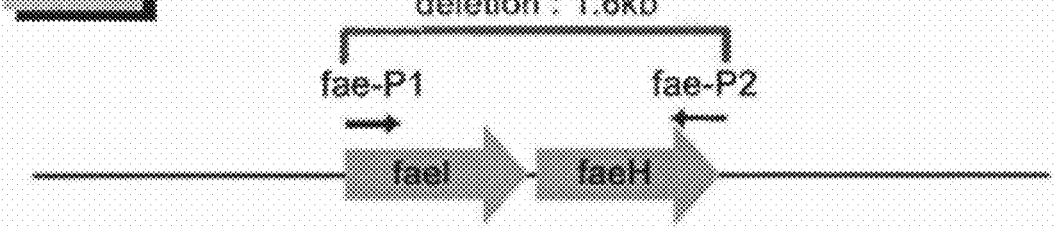
Figure 2:
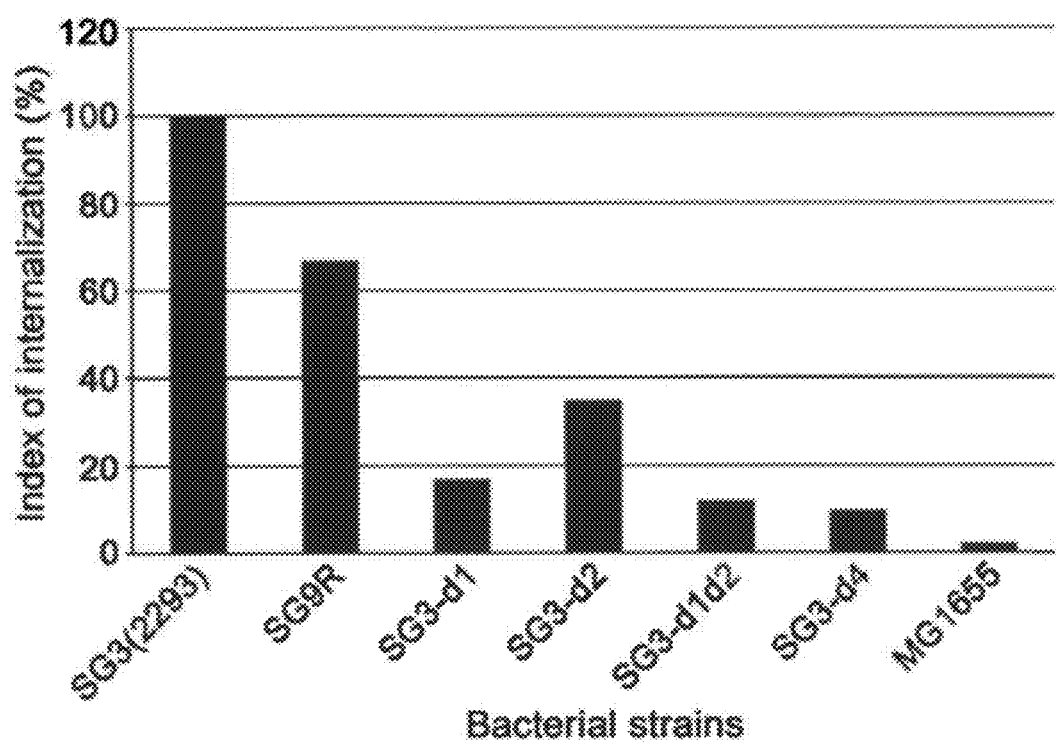
FIG. 2 is a graph showing the efficiency of the in vitro invasion into avian epithelial cells of the virulence gene-inactivated *Salmonella gallinarum* variants (SG3-d1, SG3-d2, SG3-d1d2, SG3-d4), together with controls wild-type *Salmonella gallinarum* SG2293), *Salmonella gallinarum* live vaccine (SG9R), and non-pathogenic *E. coli* (MG1655), Invasion efficiency is expressed as a percentage of the count of microorganisms within cells divided with the count of microorganisms within a culture medium. The microorganisms were used at a concentration of 8.0×10⁷ cfu per well.

In order to accomplish the above objects, an aspect of the present invention provides the avirulent *Salmonella gallinarum* variants which are remarkably decreased in pathogenicity.

The *Salmonella gallinarum* variants are rendered avirulent by inactivating at least one of the virulence gene clusters *Salmonella* pathogenicity island-1, *Salmonella* Pathogenicity Island-2, spvRABCD, and faeHI.

As used herein, the term "virulence gene clusters of *Salmonella*" refers to the four gene clusters involved in the virulence of *Salmonella gallinarum*, including the *Salmonella* Pathogenicity Island-1 (hereinafter referred to as "SPI-1") operon coding for the structural proteins and toxic effector proteins of type III secretion system, the *Salmonella* Pathogenicity Island-2 (hereinafter referred to as "SPI-2") operon coding for the structural proteins and toxic effector proteins of type III secretion system, the spvRABCD operon coding for pathogenically active proteins on avian *Salmonella*-specific virulent plasmids, and the faeHI operon coding for fimbriae. So long as it functionally works in *Salmonella gallinarum*, any gene cluster may be used.

The term "gene cluster," as used herein, refers to a population of adjacent genes on a chromosome or a plasmid that are commonly responsible for the same products. The genes in one cluster are under the regulation of common regulatory genes.

The inactivation of genes in bacteria can be achieved using various methods. For example, single or multiple nucleotides of an active site within a gene may be modified to decrease the activity of the protein expressed. Alternatively, an antibiotic-resistant gene or other gene(s) may be inserted into the gene of interest to prevent the expression of intact proteins. The most reliable method is to delete the entire sequence of a gene from the genome (Russell C B et al., J. Bacteriol. (1989); 171:2609-2613, Hamilton C M et al., J. Bacteriol. (1989); 171:4617-4622, Link A J et al., J. Bacteriol. (1997); 179: 6228-6237). In the present invention, entire sequences of the genes of interest are deleted to effectively promise the inactivation of the genes. For this, the one-step deletion method using lamda Red recombinase, known as a method of deleting gene clusters, developed by Datsenk K A et al., may be employed (Datsenko K A et al., PNAS, (2000); 97(12):6640-6645).

With regard to the information of virulence genes to be deleted, nucleotide sequences of SPI-1 and SPI-2 were obtained referring to the virulence gene sequences within the *Salmonella gallinarum* chromosome (*Salmonella enterica* subsp. *enterica* serovar *gallinarum* str. 287/91, NC 011274), disclosed by the NCBI. For the faeHI operon sequence, reference was made to the sequence of the *Salmonella gallinarum* virulence plasmid gene (*Salmonella gallinarum* virulence plasmid minor fimbrial subunit genes, AF005899). For the spvRABCD operon, the sequence of the same name gene of *Salmonella typhimurium* LT2, which has highly homology with *Salmonella gallinarum*, was consulted because its sequence is not disclosed in the NCBI. The sequencing of the spvRABCD operon of *Salmonella gallinarum* was also performed with reference to the sequence of the corresponding gene of *Salmonella typhimurium*.

Examples of the *Salmonella* virulence genes clusters include the SPI-1 gene cluster (SEQ ID NO: 1), the SPI-2 (SEQ ID NO: 2), the spvRABCD operon (SEQ ID NO: 3), and the faeHI operon (SEQ ID NO: 4) of *Salmonella gallinarum* 287/91.

To prepare strains that had definitely been rendered avirulent, all of the plural virulence gene clusters were deleted. To inactivate many gene clusters in one strain, the gene clusters may have been deleted sequentially.

In the present invention, a *Salmonella gallinarum* strain in which only the SPI-2 gene cluster is inactivated (SG3-d2), a *Salmonella gallinarum* strain in which both SPI-1 and SPI-2 gene clusters are integrally inactivated (SG3-d1d2) and a *Salmonella gallinarum* strain in which all of the four virulence gene clusters (SPI-1, SPI-2, spvRABCD, faeHI) are integrally inactivated (SG3-d4). SG3-d2 is deposited under accession No. KCCM 11009P, SG3-d1d2 under accession No. KCCM 11010P, and SG3-d4 under accession No. KCCM 11011P.

Studies on the independent deletion of individual genes of the gene clusters have been reported (Hapfelmeier S et al., J Immunol, (2005); 174(3):1675-1685, Brumme S et al., Vet Microbiol, (2007); 124(3-4):274-285, Desin T S et al., Infect Immun, July (2009); 2866-2875), but avirulent *Salmonella* strains developed by integrally inactivating two or more entire gene clusters had not been disclosed prior to the study of the present inventors. The *Salmonella gallinarum* strain was named *Salmonella gallinarum* SG2293-d2 when only the SPI-2 gene cluster is inactivated, and SG2293-d1d2 when both SPI-1 and SPI-2 were integrally inactivated. Further, it was named SG2293-d4 upon the inactivation of all of SPI-1, SPI-2, spvRABCD, and faeHI.

To ascertain the avirulence thereof, the strains prepared by inactivating virulence gene clusters according to the present invention were assayed for the efficiency of invasion into avian epithelial cells and for disease outbreak and mortality (%) upon infection into poultry. Preferably, the *Salmonella gallinarum* strains in which the virulence gene clusters had been inactivated by transformation were allowed to invade avian epithelial cells so that invasion efficiency could be measured. Also, the strains were injected into brown egg layers to measure mortality.

In accordance with another aspect thereof, the present invention provides an avirulent *Salmonella* strain for use in producing *Salmonella*-specific lytic bacteriophages and a method for producing phages using the same.

ΦCJ1 (US 20100135962), a *Salmonella*-specific phage, was used to examine the bacteriophage productivity of the avirulent *Salmonella gallinarum* variants. The phage shows a specific bactericidal activity against *Salmonella gallinarum* and *Salmonella pullorum*, belongs to the morphotype group of the family Siphoviridae B1, characterized by isometric capsid and long non-contractile tail, and has a total genome size of 61 kb and major structural proteins with a size of 38 kDa and 49 kDa.

The method for producing a bacteriophage in accordance with the present invention comprises culturing the avirulent *Salmonella gallinarum* variants in a medium, inoculating a bacteriophage into the medium, and recovering the bacteriophage. In this regard, the phage may be produced briefly using a plate or on a mass scale using broth. In the case of production using a plate, a bacteriophage is inoculated at a suitable ratio into bacteria when the bacteria enter a log phase, mixed with top agar, and poured onto a plate. When phage plaques appear, the top agar fractions are collected and centrifuged, followed by filtering the supernatant to afford a phage stock. For mass production as a broth, a mixture of phages and bacteria is prepared in the same manner as in plate production, and incubated for 5 hours in fresh broth, instead of in top agar.

In accordance with a further aspect thereof, the present invention provides a pharmaceutical composition for the prevention of fowl typhoid, comprising the avirulent *Salmonella* strain as an active ingredient and optionally a pharmaceutically acceptable vehicle, and preferably a vaccine for the prevention of fowl typhoid, formulated with the avirulent *Salmonella* strain and optionally a pharmaceutically acceptable vehicle.

The term "pharmaceutically acceptable vehicle," as used herein, refers to a carrier or diluent which does not deteriorate the biological activity and property of the active ingredient and which does not irritate the subject. Preparations intended for oral administration may take the form of tablets, troches, lozenges, aqueous or oily suspensions, powders, granules, emulsions, hard or soft capsules, syrups, elixirs, etc. In regards to the oral forms such as tablets and capsules, the active ingredient may be formulated in combination with a binder such as lactose, saccharose, sorbitol, mannitol, starch, amylpectin, conjugate such as cellulose or gelatin, an excipient such as dicalcium phosphate, a disintegrant such as corn starch or sweet potato starch, or a lubricant such as magnesium stearate, calcium stearate, sodium stearylfumarate or polyethylene glycol wax. As for capsules, they may further comprise a liquid carrier such as fatty oil.

The composition of the present invention may be formulated into preparations for non-oral administration, such as subcutaneous injections, intravenous injections, or intradermal injections. For this, the composition of the present invention may be mixed with a stabilizer or buffer in water to give a solution or a suspension which is then formulated into unit doses such as ampules or vials.

As used herein, the term "vaccine" refers to a biological preparation that improves immunity to a particular disease by inducing the formation of an antibody upon injection into the body, a preparation containing an antigen, e.g., killed or attenuated forms of a disease-causing microorganism. Vaccines may be prepared from killed pathogens. There are also live vaccines, but with the virulence thereof attenuated. The *Salmonella gallinarum* variants of the present invention have the same antigenic proteins as those of the wild-type, but are greatly decreased in virulence compared to the wild-type, so that they can be used as live vaccines prophylactic of fowl typhoid.

In accordance with still another aspect thereof, the present invention provides a feedstuff containing the avirulent *Salmonella gallinarum*, and preferably a feed additive containing the avirulent *Salmonella gallinarum*. When applied to poultry, the feed additive of the present invention serves as a live vaccine that prevents fowl typhoid.

The feedstuff of the present invention may be prepared by mixing feedstuff with the *Salmonella gallinarum* variant as it is or in the form of a feed additive. In the feedstuff, the *Salmonella gallinarum* variant may be in a liquid or dry state. The dry state can be accomplished by various drying methods including, but not limited thereto, pneumatic drying, spontaneous drying, spray drying and freeze drying. In addition to the *Salmonella gallinarum* variant of the present invention, the feedstuff of the present invention may further comprise a typical additive useful for improving the preservation of the feedstuff.

The feedstuff comprising the *Salmonella gallinarum* variant of the present invention may be vegetable matter such as a cereal, nut, a by-product of food processing, millet, fiber, pharmaceutical by-product, a vegetable oil, starch, oil seed meals and cereal remnants, or animal matter such as proteins, minerals, fats, mineral oils, unicellular proteins, animal planktons and leftover food etc.

Examples of the feed additive comprising the *Salmonella gallinarum* variant of the present invention include, but are not limited to, various agents for preventing quality deterioration and improving utility, such as binders, emulsifiers, preservatives, amino acids, vitamins, enzymes, probiotics, flavoring agents, non-protein nitrogen compounds, silicates, buffer, colorants, extracts, oligosaccharides, etc. Also, a mixing agent may be within the scope of the feed additive.

In accordance with still a further aspect thereof, the present invention provides a method for treating the *Salmonella gallinarum* infectious disease fowl typhoid using the pharmaceutical composition.

The composition of the present invention may be administered to animals in the form of a pharmaceutical preparation to animals, or in the form of being mixed with feedstuff or water. Preferably, it is mixed in the form of a feed additive with feedstuff before administration.

So long as it allows the composition of the present invention to reach tissues or cells of interest, any administration route, such as non-oral, intraartery, intradermal, transdermal, intramuscular, intraperitoneal, intravenous, subcutaneous, oral or intranasal route, may be taken.

The treating method of the present invention comprises administering the composition of the present invention in a pharmaceutically effective amount. It will be apparent to those skilled in the art that the suitable total daily dose may be determined by an attending physician within the scope of medical judgment. The specific therapeutically effective dose level for any particular patient may vary depending on a variety of factors, including the kind and degree of desired reaction, the specific composition, including the use of any other agents according to the intended use, the patient's age, weight, general health, gender, and diet, the time of administration, the route of administration, and rate of the excretion of the composition; the duration of the treatment; other drugs used in combination or coincidentally with the specific composition; and like factors well known in the medical arts. Typically, the composition may be administered at a daily dose of from $10^4$ to $10^8$ CFU once or in a divided dosage manner.

Hereinafter, the present invention will be described in more retail with reference to Examples. However, these Examples are for illustrative purposes only, and the invention is not intended to be limited by these Examples.

EXAMPLE 1

Screening of Target Genes to be Inactivated Through Comparison of *Salmonella gallinarum* Virulence Genes The first step of preparing avirulent avian *Salmonella* strains was the screening of target virulence genes to be inactivated. *Salmonella* Pathogenicity Island-1 (SPI-1), and *Salmonella* Pathogenicity Island-2 (SPI-2), both of which are type three secretion system gene clusters essential for the delivery of the pathogenicity of *Salmonella*, and spvRABCD and faeHI, both of which are genes on virulence plasmids, were determined as target genes, and the data base of the NCBI was searched for the nucleotide sequences of the target genes (*Salmonella enterica* subsp. *enterica serovar gallinarum* str. 287/91, NC 011274). Because the nucleotide sequence of spvRABCD of *Salmonella gallinarum* had not yet been disclosed, primers were synthesized with reference to the nucleotide sequence of the same name gene of *Salmonella typhimurium* (*Salmonella typhimurium* LT2 plasmid pSLT, NC 003277), which has high nucleotide sequence homology with *Salmonella gallinarum*. As for the faeHI operon, the information of its nucleotide sequence was obtained from *Salmonella gallinarum* virulence plasmid minor fimbrial subunit genes (AF005899).

EXAMPLE 2

Preparation of Avirulent Variants by Inactivation of Virulence Genes of *Salmonella gallinarum* and by Integration of the Inactivated Sites 2-1. Inactivation of Virulence Genes of *Salmonella gallinarum*

To delete TTSS-related virulence genes of the wild-type *Salmonella gallinarum* (SGSC No. 2293) as determined in Example 1, the one-step deletion method using lamda Red recombinase, developed by Datsenko K A et al., (Datsenko K A et al, PNAS, (2000); 97(12):6640-6645), was employed.

A chloramphenicol resistant gene of pKD3 was used as an antibiotic marker for identifying insertion into a target site of chromosome. Using a pair of the primers SPI-1-P1 (SEQ ID NO: 5) and SPI-1-P2 (SEQ ID NO: 6) of Table 1, which correspond to 50 bp of 5' flanking region of the avrA and 50 bp of 3' flanking region of the invH gene, wherein SPI-1 comprising from avrA to invH is target for deletion, and a part of the chloramphenicol resistant gene of pKD3, respectively, a polymerase chain reaction (hereinafter referred to as "PCR") was performed [Sambrook et al, Molecular Cloning, a Laboratory Manual (1989), Cold Spring Harbor Laboratories], with pKD3 as a template. The obtained PCR product was gene fragment about 1100 bp long.

In this regard, a PCR HL premix kit (BIONEER) was used and 30 cycles of denaturation at 94° C. for 30 sec, annealing at 55° C. for 30 sec and elongation at 72° C. for 1 min was conducted. The PCR product was separated in 0.8% agarose gel by electrophoresis and eluted at a desired band size.

According to the method of Datsenko K A et al., the 1100 bp-long gene fragment was introduced into pKD46-transformed, competent wild-type *Salmonella gallinarum*, which was then spread over LB plates containing chloramphenicol (30 mg/L). As for the resulting transformant, its gene was examined by PCR using a pair of the primers SPI-1-P3 (SEQ ID NO: 7) and SPI-1-P4 (SEQ ID NO: 8), which correspond to regions about 1 kb distant from both ends of the deletion target gene, respectively. The PCR product thus obtained was 3100 bp long, indicating that the SPI-1 gene cluster was inactivated.

The resulting strain was cultured at 37° C., a condition of removing the pKD46 vector, to select a strain that could not grow on an LB plate containing ampicillin (100 mg/L).

Subsequently, the antibiotic marker inserted into the inactivated gene cluster was removed by transformation with pCP20. The removal of the antibiotic marker was identified by PCR using the primers SPI-1-P3 & SPI-1-P4. The resulting PCR product was 2000 bp long, also indicating the inactivation.

Afterwards, the strain which was now free of the antibiotic marker was cultured at 42° C. (a condition of removing pCP20) to select a strain that could not grow on an LB plate containing ampicillin. The SPI-1 gene cluster-inactivated strain thus obtained was named SG3-d1 (*Salmonella gallinarum* SG2293::ΔSPI-1).

SPI-2, spv, and fae gene clusters were also inactivated in the same manner as in the SPI-1 gene cluster. The resulting gene cluster-inactivated strains were named SG3-d2 (*Salmonella gallinarum* SG2293::ΔSPI-2, Accession No. KCCM 11009P), SG3-ds (*Salmonella gallinarum* SG2293::Δspv), and SG3-df (*Salmonella gallinarum* SG2293::Δfae), respectively. Primers used for deleting genes and for identifying gene deletion are summarized in Table 2, below.

TABLE 2

Primers for deletion of SPI-1 gene from chromosome

| | | |
|---|---|---|
| SPI-1-P1 | (SEQ ID NO: 5) | TTATGGCGCTGGAAGGATTTCCTCTGGCAGGCAACCT TATAATTTCATTAGTGTAGGCTGGAGCTGCTTC |
| SPI-1-P2 | (SEQ ID NO: 6) | ATGCAAAATATGGTCTTAATTATATCATGATGAGTTC AGCCAACGGTGATCATATGAATATCCTCCTTAG |

Primers for Deletion of SPI-2 Gene from Chromosome

| | | |
|---|---|---|
| SPI-2-P1 | (SEQ ID NO: 9) | ACCCTCTTAACCTTCGCAGTGGCCTGAAGAAGCATAC CAAAAGCATTTATGTGTAGGCTGGAGCTGCTTC |
| SPI-2-P2 | (SEQ ID NO: 10) | ACTGCGTGGCGTAAGGCTCATCAAAATATGACCAATG CTTAATACCATCGCATATGAATATCCTCCTTAG |

Primers for Deletion of spvRABCD gene from virulence plasmid

| | | |
|---|---|---|
| spv-P1 | (SEQ ID NO: 13) | GTGCAAAAACAGGTCACCGCCATCCTGTTTTTGCACA TCAAA ACATTTTGTGTAGGCTGGAGCTGCTTC |
| spv-P2 | (SEQ ID NO: 14) | TTACCCCAACAGCTTGCCGTGTTTGCGCTTGAACATA GGGAT GCGGGCTTCATATGAATATCCTCCTTAG |

Primers for Deletion of faeHI gene from virulence plasmid

| | | |
|---|---|---|
| fae-P1 | (SEQ ID NO: 17) | TTACCGATATTCAATGCTCACCGCCAGGGAGGTATGC CAGCG GGACGGTAGTGTAGGCTGGAGCTGCTT C |
| fae-P2 | (SEQ ID NO: 18) | ATGAAAATAACGCATCATTATAAATCTATTATTTCCG CC CTGGCCGCGCTCATATGAATATCCTCCTTAG |

TABLE 2-continued

Primers for identification of SPI-1 gene deletion from chromosome

| | | |
|---|---|---|
| SPI-1-P3 | (SEQ ID NO: 7) | ATGTTCTTAACAACGTTACTG |
| SPI-1-P4 | (SEQ ID NO: 8) | AGGTAGTACGTTACTGACCAC |

Primers for identification of SPI-2 gene deletion from chromosome

| | | |
|---|---|---|
| SPI-2-P3 | (SEQ ID NO: 11) | TGTTCGTACTGCCGATGTCGC |
| SPI-2-P4 | (SEQ ID NO: 12) | AGTACGACGACTGACGCCAAT |

Primers for spvRABCD gene deletion from virulence plasmid

| | | |
|---|---|---|
| spv-P3 | (SEQ ID NO: 15) | GACCATATCTGCCTGCCTCAG |
| spv-P4 | (SEQ ID NO: 16) | CAGAGCCCGTTCTCTACCGAC |

Primers for faeHI gene deletion from virulence plasmid

| | | |
|---|---|---|
| fae-P3 | (SEQ ID NO: 19) | CAGGCTCCCCTGCCACCGGCT |
| fae-P4 | (SEQ ID NO: 20) | CAGGCCAACTATCTTTCCCTA |

2-2. Integration of Type III Secretion System-Related Virulence Genes Inactivation To integrally inactivate the gene clusters in one strain, the SG3-d1 strain was sequentially subjected to the inactivation of SPI-2, spvRABCD, and faeHI gene clusters, using a method similar to that of Example 2-1.

To begin with, PCR was performed using the primers SPI-2-P1 (SEQ ID NO: 9) and SPI-2-P2 (SEQ ID NO: 10) for the purpose of inactivating the SPI-2 cluster gene, with pKD4 serving as a template, resulting a 1600 bp gene fragment. This PCR product was introduced into the SG3-d1 strain in which pKD46 vector remained (Example 1-2), followed by spreading the bacteria over an LB plate containing kanamycin (50 mg/L). As for the resulting transformant, its gene was examined by PCR using a pair of the primers SPI-2-P3 (SEQ ID NO: 11) and SPI-2-P4 (SEQ ID NO: 12), which correspond to both flanking regions of the deletion target gene. The PCR product thus obtained was 3600 bp long, indicating that the SPI-2 gene cluster was inactivated.

The resulting strain was cultured at 37° C., a condition of removing the pKD46 vector, to select a strain that could not grow on an LB plate containing ampicillin (100 mg/L).

Subsequently, the antibiotic marker inserted into the inactivated gene cluster was removed by transformation with pCP20. The removal of the antibiotic marker was identified by PCR using the primers SPI-1-P3 & SPI-1-P4 in case of SPI-1 and the primers SPI-2-P3 & SPI-2-P4 in case of SPI-2. The resulting PCR product was 2000 bp long, also indicating that the inactivation had taken place.

Afterwards, the strain free of the antibiotic marker was cultured at 42° C. (a condition of removing pCP20) to select a strain that could not grow on an LB plate containing ampicillin. The SPI-1 and SPI-2 gene cluster-inactivated strain thus obtained was named SG3-d1d2 (*Salmonella gallinarum SG*2293::ΔSPI-1ΔSPI-2, Accession No. KCCM 11010P).

In SG-d1d2 strain, spvRABCD and faeHI gene clusters were further inactivated. To this end, the spvRABCD gene cluster (the kanamycin-resistant gene of pKD4 was used as an antibiotic marker) was inactivated in the same manner as in the inactivation of SPI-1 in Example 1-2, while the inactivation of the faeHI gene cluster (the chloramphenicol-resistant gene of pKD3 was used as an antibiotic marker) was conducted in the same manner as in the inactivation of SPI-2 in the SPI-1-inactivated strain. As for the resulting transformants, their genes were examined by PCR using the primer set spv-P3 (SEQ ID NO: 15) and spv-P4 (SEQ ID NO: 16) for spvRABCD deletion, and the primer set fae-P3 (SEQ ID NO: 19) and fae-P4 (SEQ ID NO: 20) for faeHI deletion, which correspond to regions about 1 kb distant from both ends of the respective deletion target genes. The PCR products thus obtained were 3600 bp, 3100 bp long respectively, indicating that the spvRABCD and faeHI gene clusters were inactivated. The resulting strain was cultured at 37° C., a condition of removing the pKD46 vector, to select a strain that could not grow on an LB plate containing ampicillin (100 mg/L). The *Salmonella gallinarum* strain in which all of the four gene clusters SPI-1, SPI-2, spvRABCD and faeHI were integrally inactivated was named SG3-d4 (*Salmonella gallinarum* SG2293::ΔSPI-1ΔSPI-2ΔspvRABCDΔfaeHI) and deposited under accession No. KCCM 11011P.

2-3. Sequencing of *Salmonella gallinarum* spvRABCD Operon

Nowhere has the genetic information on spvRABCD of *Salmonella gallinarum* (SGSC No. 2293) been disclosed yet. Its nucleotide sequence was analyzed in the present invention. For this, primers were synthesized as summarized in Table 3, below.

TABLE 3

| | |
|---|---|
| spv-S1 (SEQ ID NO: 21) | GGTCAATTAAATCCACTCAGAA |
| spv-S2 (SEQ ID NO: 22) | ACGGGAGACACCAGATTATC |
| spv-S3 (SEQ ID NO: 23) | TTCAGTAAAGTGGCGTGAGC |
| spv-S4 (SEQ ID NO: 24) | CCAGGTGGAGTTATCTCTGC |
| spv-S5 (SEQ ID NO: 25) | ACTGTCGGGCAAAGGTATTC |
| spv-S6 (SEQ ID NO: 26) | TTTCTGGTTACTGCATGACAG |
| spv-S7 (SEQ ID NO: 27) | TCCAGAGGTACAGATCGGC |
| spv-S8 (SEQ ID NO: 28) | GAAGGAATACACTACTATAGG |
| spv-S9 (SEQ ID NO: 29) | GTGTCAGCAGTTGCATCATC |

TABLE 3-continued

| | | |
|---|---|---|
| spv-S10 | (SEQ ID NO: 30) | AGTGACCGATATGGAGAAGG |
| spv-S11 | (SEQ ID NO: 31) | AAGCCTGTCTCTGCATTTCG |
| spv-S12 | (SEQ ID NO: 32) | AACCGTTATGACATTAAGAGG |
| spv-S13 | (SEQ ID NO: 33) | TAAGGCTCTCTATTAACTTAC |
| spv-S14 | (SEQ ID NO: 34) | AACCGCTTCTGGCTGTAGC |
| spv-S15 | (SEQ ID NO: 35) | CCGTAACAATGACATTATCCTC |

The analysis result is given in SEQ ID NO: 3.

EXAMPLE 3

Assay of Virulence Gene-Inactivated *Salmonella gallinarum* SG2-d4 for Avirulence by Measurement of Invasion Efficiency into Avian Epithelial Cell

*Salmonella gallinarum* and *Salmonella pullorum*, which are unique *Salmonella* species due to the lack of a motile flagella, are specifically infected to avian cells and can invade other animal cells but at very low efficiency. In this example, an in vitro cell invasion assay was conducted (Henderson S C et al, Infect Immun, (1999); 67(7):3580-3586) on the avian epithelial cell line BAT (Budgerigar Abdominal Tumor), provided from MD. Lee, Georgia University. The avirulent *Salmonella gallinarum* variants SG3-d1d2 and SG3-d4, developed by the above-described gene deletion method, were expected to invade the host cell with very low efficiency by reduced level of TTSS-related protein. A recent research review on the infection mechanisms of pathogenic microorganisms has it that even when only a specific gene of SPI-1 is deleted, the *Salmonella* strain shows a decrease in invasion efficiency into epithelial cells (Lostroh C P et al, Microbes Infect, (2001); 3(14-15):1281-1291).

In the present invention, TTSS-related gene deletion was proven to lead to a decrease in virulence by measuring the efficiency of the invasion of the avian *Salmonella* variants into the avian epithelial cell line BAT.

Invasion efficiency into avian epithelial cells was measured on 24-well plates in triplicate, and mean values of three measurements were given. The BAT cell line was cultured at 37° C. in DMEM supplemented with 10% fetal bovine serum, 1 mM glutamine, 100 IU/ml penicillin and 100 μg/ml streptomycin under the condition of 5% $CO_2$. The BAT cell line was seeded at a density of $2.5\times10^5$ cells/well into 24-well plates and incubated at 37° C. for 1~2 days in a 5% $CO_2$ incubator to form monolayers of cells. After distribution of the cell and incubation for one day, the culture medium was changed out with antibiotic-free DMEM. For comparison of invasion efficiency, wild-type *Salmonella gallinarum* SG3 (SGSC#: 2293), the virulence gene-inactivated *Salmonella gallinarum* variants SG3-d1, SG3-d2, SG3-d1d2 and SG3-d4, and SG9R, which is a commercially available live vaccine, were employed, with the non-pathogenic *E. coli* MG1655 serving as a control.

After being primarily seed cultured, all of test bacteria were vigorously incubated for 4~5 hours in a main LB medium, and the cultures were diluted to $OD_{600}$=1.0. To 200 μL of the animal cells incubated in the antibiotic-free medium, 200 μL of each of the culture dilutions was added so that the bacteria were aliquoted at a concentration of $2.0\times10^8$ cfu/ml per well. The plates were incubated at 37° C. for one hour in a 5% $CO_2$ atmosphere to allow the bacteria to penetrate into the epithelial cells. Thereafter, the medium was aspirated off and the plates were washed with 1×PBS to remove remaining microorganisms. Then, the epithelial cells were incubated at 37° C. for 2 hours in the presence of 50 μg/ml gentamycin in a 5% $CO_2$ incubator to clear the microorganisms remaining outside the cells. The antibiotic was removed by washing with 1×PBS. To examine the microorganisms which succeeded in penetrating into the epithelial cells, the animal cells were lyzed for 15~30 min in 500 μl of 0.1% Triton X-100. The cell lysates were spread over LB plates and incubated overnight at 37° C. so that the microorganisms that had grown could be counted. To calculate the invasion efficiency, 200 μL of the microorganism culture with $OD_{600}$=1.0 was also incubated.

Invasion Efficiency(%)=Count of Microorganisms Invaded to Cell/Count of Microorganisms within Culture Medium($OD_{600}$=1.0)×100

The BAT cell invasion efficiencies of the four transformed *Salmonella gallinarum* variants prepared by the inactivation of virulence gene clusters were calculated.

Of them, the variant in which only the SPI-1 gene cluster, responsible for cell invasion mechanism, was inactivated, was decreased in invasion efficiency by 84% compared to the wild-type. The SG3-d1d2 variant with the deletion of both SPI-1 and SPI-2 and the SG3-d4 variant with the deletion of all the four gene clusters were found to decrease in cell invasion efficiency by approximately 89% and 91%, respectively, compared to the wild-type *Salmonella gallinarum* (SG3). The variants of the present invention were also remarkably reduced in invasion ability, in comparison to that of the commercially available live vaccine Nobilis SG9R. These data demonstrated that the inactivation of TTSS-related gene clusters decreases the virulence of *Salmonella gallinarum* (see Table 4 and FIG. 2).

TABLE 4

| | Strain | Property | Genotype | Index of Internalization (%) |
|---|---|---|---|---|
| Control Group | MG1655 | Avirulent *E. coli* | Wild type | 2% |
| | SG3 | Virulent *Salmonella Gallinarum* (Wild-type, SGSC No. 2293) | Wild type | 100% |
| | *Nobilis* SG9R | *Salmonella Gallinarum* Live vaccine (commercially available) | SG:: ΔrecA | 67% |
| Test Group (avirulent *Salmonella Gallinarum*) | SG3-d1 | Virulence gene-deleted *Salmonella Gallinarum* | SG:: ΔSPI-1 | 16% |
| | SG3-d2 | Virulence gene-deleted *Salmonella Gallinarum* | SG:: ΔSPI-2 | 34% |
| | SG3-d1d2 | Virulence gene-deleted *Salmonella Gallinarum* | SG:: ΔSPI-1/ΔSPI-2 | 11% |
| | SG3-d4 | Virulence gene-deleted *Salmonella Gallinarum* | SG:: ΔSPI-1/ΔSPI-2/Δspv/Δfae | 9% |

(SG3 100% = 0.36% invasion efficiency in practice)

The avirulence of *Salmonella gallinarum* variant SG3-d4 was confirmed in vitro test which shows extremely low in invasion efficiency into avian epithelial cells, as was reconfirmed in animal tests and the results are given in Example 4.

EXAMPLE 4

Assay of *Salmonella gallinarum* SG3-d4 for Avirulence by Measuring Mortality of Chickens The Research Institute of Veterinary Science, Seoul National University, was entrusted with this assay. One-week-old brown egg layers (Hy-Line chicken) were employed in this assay, and they were divided into many groups of 10 which were separated in respective chicken houses before infection with pathogens. No vaccine programs were used on the experimental animals after they hatched.

Five avian *Salmonella* strains including the wild-type *Salmonella gallinarum* SG3 (SGSC#: 2293), the virulent gene cluster-inactivated *Salmonella gallinarum* SG3-d2 and SG3-d4 (identified to decrease in virulence by in vitro invasion assay), the commercially available live vaccine Nobilis SG9R, and the non-pathogenic *E. coli* MG1655 were employed in the in vivo assay.

After being primarily seed cultured, the five strains were vigorously incubated for 4~5 hours to $OD_{600}$=1.0 in a main LB medium, and the concentration of each of the cell cultures was adjusted to $1.0 \times 10^8$ cfu/ml. The bacteria was subcutaneously injected at an adjusted dose into the chickens which were the monitored for two weeks for mortality. Subsequently, the chickens which were alive were autopsied to examine lesions and to isolate bacteria.

For the two weeks after artificial infection of the pathogens ($1.0 \times 10^8$ cfu/mL), the chickens infected with *Salmonella gallinarum* (SG3) were observed and showed typical external syndromes such as low motility, blue diarrhea and low uptake of feedstuff, and looked to be dying. The mortality was not high, but an autopsy disclosed lesions in almost all the chickens.

In contrast, the chicken group infected with the *Salmonella gallinarum* variant (SG3-d4) the avirulence of which was proven by in vitro invasion assay were observed to actively move and not die although some of them had diarrhea during the two weeks. Also, they were found to have almost no lesions in the autopsy. Therefore, the *Salmonella gallinarum* variant of the present invention was again proven to have greatly decreased virulence. The chicken groups infected with the SG3-d2 variant in which the gene responsible for primary invasion into host cells remains intact while the SPI-2 gene involved in systemic infection and survival over phagocytosis is inactivated, or with the SG3-ds variant in which the spv gene known to participate in pathogenicity is inactivated, were observed to have low or no mortality (%). Thus, even the inactivation of single gene clusters had a great influence on the reduction of pathogenicity (see Table 5).

TABLE 5

| | Strain | Property | Geno-type | Mortality (%) | Frequency of lesions in live birds (%) |
|---|---|---|---|---|---|
| Control Group | MG1655 | Avirulent *E. coli* | Wild-type | 0% | 20% (2/10) |
| | SG3 | Virulent *Salmonella Gallinarum* | Wild-type | 20% | 88% (7/8) |
| | Nobilis SG9R | (Wild-type, SGSC No. 2293) *Salmonella Gallinarum* Live vaccine (commercially available) | SG::ΔrecA | 0% | 40% (4/10) |
| Test Group (avirulent *Salmonella Gallinarum*) | SG3-d1 | Virulence gene-deleted *Salmonella Gallinarum* | SG::ΔSPI-1 | 40% | 17% (1/6) |
| | SG3-d2 | Virulence gene-deleted *Salmonella Gallinarum* | SG::ΔSPI-2 | 10% | 0% (0/9) |
| | SG3-ds | Virulence gene-deleted *Salmonella Gallinarum* | SG::Δspv | 0% | 20% (2/10) |
| | SG3-d4 | Virulence gene-deleted *Salmonella Gallinarum* | SG::ΔSPI-1/ ΔSPI-2/ Δspv/ Δfae | 0% | 10% (1/10) |

According to autopsy findings, the liver and spleen were swollen and weakened, with the significant frequency of greenish brown or bluish green liver lesions, in the chicken group infected with the wild-type *Salmonella gallinarum* (SG3). Like the commercially available live vaccine Nobilis SG9R or the non-pathogenic *E. coli* MG1655, however, the virulent gene cluster-inactivated variants of the present invention (SG3-d1d2 and SG3-d4) were found to produce almost no lesions, and were demonstrated to be harmless to chickens.

EXAMPLE 5

Comparison of the Productivity of ΦCJ1 Bacteriophage Specific to *Salmonella gallinarum* Variants Ultimately, the development of avirulent *Salmonella* stains is to apply to the production of *Salmonella*-specific lytic bacteriophages. The *Salmonella* variants prepared in Example 2 were proven to have greatly attenuated virulence in Examples 3 and 4. Finally, ΦCJ1 (Korean Patent Application No. 10-2008-121500/US20100135962), which specifically infects avian *Salmonella*, was used to examine a difference in bacteriophage productivity between the wild-type and the avirulent *Salmonella gallinarum* variants.

The avian-specific bacteriophage ΦCJ1 was cultured on a mass scale, with the wild-type *Salmonella gallinarum* strain (SG3) or the variant serving as a host cell. For this, each bacterial strain was cultured to an $OD_{600}$ of 0.5 ($2.5 \times 10^{10}$ colony forming units (cfu)) in 50 mL of LB broth in a flask with agitation. ΦCJ1 was inoculated at $1.25 \times 10^9$ pfu (plaque forming unit) to form an MOI (multiplicity of infection) of 0.05, and allowed to stand for 20 min at 37° C., followed by additional incubation at 37° C. for 4 hours. Chloroform was added in an amount of 2% of the final volume and shakes for 20 min. After passage of the supernatant through a 0.2 μm filter, the titer of ΦCJ1 was counted.

ΦCJ1 was produced at a titer of $6 \times 10^{11}$ pfu/ml from the wild-type strain (SG3) and at a titer of $8 \times 10^{10}$ pfu/ml from the avirulent *Salmonella gallinarum* variant (SG3-d4). These data demonstrated that the avirulent variants prepared by inactivating virulence gene clusters have no problems with infection with bacteriophages and can be used as host cells for producing bacteriophages (see Table 6). In addition, ΦCJ2 (US 20100158870) and ΦCJ3 (US 20100166709), which were both developed by the same applicant, were produced using the variant as a host cell. The host cell was found to allow the production of ΦCJ2 at a titer of approximately $2\times10^{10}$ pfu/ml and ΦCJ3 at a titer of approximately $5\times10^{9}$ pfu/ml. Like ΦCJ1, ΦCJ2 and ΦCJ3 were produced from the variant of the present invention, without significant difference from the wild-type.

TABLE 6

| | Strain | Property | Genotype | Production Titer of ΦCJ1 (pfu/ml) |
|---|---|---|---|---|
| Control Group | SG3 | Virulent *Salmonella Gallinarum* (Wild-type, SGSC No. 2293) | Wild type | $6\times10^{11}$ |
| Test Group (avirulent *Salmonella Gallinarum*) | SG3-d4 | Virulence Gene-Deleted *Salmonella Gallinarum* | SG3::ΔSPI-1/ΔSPI-2/Δspv/Δfae | $8\times10^{10}$ |

As described hitherto, the avirulent *Salmonella gallinarum* variants, prepared by inactivating virulence genes, according to the present invention are useful as host cells for effectively producing *Salmonella*-specific lytic bacteriophages on an industrial scale with the advantage of cost saving. The avirulent *Salmonella gallinarum* variants simplify the purification process taken to remove toxicity after bacteriophage production, thus greatly reducing the production cost and solving the safety problem of the products. In addition, the variants can be used as live vaccines that guarantee higher immunological effects and safety than do conventional vaccines.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An isolated modified *Salmonella gallinarum*, comprising inactivated gene clusters of *Salmonella* Pathogenicity Island-1, *Salmonella* Pathogenicity Island-2, spvRABCD, and faeHI, wherein inactivation of the gene clusters is carried out using a method selected from the group consisting of a modification of single or plural nucleotides in the gene, deletion of single or plural genes, insertion of an exogenous gene into the genes, deletion of all of the gene clusters, and combinations thereof.

2. The isolated modified *Salmonella gallinarum* of claim 1, wherein *Salmonella* Pathogenicity Island-1 of SEQ ID NO: 1, *Salmonella* Pathogenicity Island-2 of SEQ ID NO: 2, spvRABCD of SEQ ID NO: 3, and faeHI of SEQ ID NO: 4 have been deleted (SG3-d4).

3. The isolated modified *Salmonella gallinarum* of claim 2, deposited under accession No. KCCM 11011P.

4. A pharmaceutical composition for treatment of fowl typhoid, comprising the isolated modified *Salmonella gallinarum* of claim 1 as an effective ingredient.

5. The pharmaceutical composition of claim 4, wherein the composition is a vaccine.

6. A feed additive, comprising the isolated modified *Salmonella gallinarum* of claim 1 as an effective ingredient.

7. A method for producing bacteriophage, comprising: culturing the isolated modified *Salmonella gallinarum* of claim 1 in a culture medium; inoculating the bacteriophage into the culture medium; and recovering bacteriophage progeny from the culture medium.

* * * * *

SEQUENCE LISTING

<160> NUMBER OF SEQ ID NOS: 35

<210> SEQ ID NO 1
<211> LENGTH: 34934
<212> TYPE: DNA
<213> ORGANISM: Artificial Sequence
<220> FEATURE:
<223> OTHER INFORMATION: Salmonella pathogenicity island-1

<400> SEQUENCE: 1

```
ttacgattta agtaaagact tatattcagc tatccttttt ttatgagcgg atatagagag     60 tttttttatcg tttagcataa cggcattgtt atcgaatcgc tcataaagcg tttcattctt    120
tttgtttact atactgcttc ccgccgccgg attggcctcc acatattcat ttaatcgttg    180
tacgccttga gtatgtttgt aaaaactcac cggcagataa cggtctgctt tatcggacgg    240
gagaaaaggt tcttcaccac acagacgttc acaaatatta tcttcatgaa tttttactaa    300
gttcataaat tcaagctgaa gttttttggc gagcgccagg ctaaaaatac cgcattcaga    360
agagcttcgt tgaatgtcca gctcgaccat agcaaaataa caatcaggca gttgttcacg    420
ttcaagagct gctttggtcc tcaacgccag taaagcaggt ccaaaagcgc tacacgctgc    480
tggttcgaac aaaatcaccg atgtctttcc gtccataact ctaaaatcga cgactgaaat    540
atggatacct gaacttccca tatttacgag aaatcgggca gattcaacgc cttccattct    600
ggtctccttt atagaggaaa caagctcatg gactgacata acaaatttaa gatttaactc    660
tggatacttc ttattggcct gtgcaacaag aaaaggcatc atttcgagat cggtttcctc    720
gtaactgata tgaatccagc tgccatctat aatttcactt tccagacgct caacaataca    780
ggtcaatgct tcggtgttta gctccccgct gacgtcaggc tgaggcgata aactcgcccc    840
catattacga gtcgtaggac ttagcatact tttccctcca catgatagct cctgcaccga    900
aaatatcatc tttaactttt cagattcaat atattgcctg caaaaatatg cctcaatgat    960
```

```
tgagccaggc taccaaccac ctccggatga ttatatataa gaattactac tcaaaaaatc    1020 tttttttataa taaaagctca acacatggtc ataaatgata aaaaatattt taattcattc    1080
ctaccgcaat cggtaacgcg caattatcgt caggtacagc agggttatgt gcaaaagcag    1140
tgcgctgtaa atgcgcgtct agtttcagtc cccggaacag cgatagcggt gaagagtcca    1200
tccccaaacg atacataacc ttcttacgat aaatactgac ggttttttgtt cccagaccaa    1260 attttttcgc cagttcaatt gccggatgtc cggaggataa taatatcagc agcgcatatt    1320
tcgcctgcgt gacaccggga ggtagattcc accaggcgta ttgattgata ttaaacaata    1380
cctcttccgg cgtctcgccg gcattaaaag catacgtagc agccacggtt ttcttttgtg    1440
gcctgtggca gaaacgcagc caggcttccg gaagacggag cttctctcgc tccgagcgga    1500
tagcgcagga tagttcgtct tttaaaacat aatccataac gccaaaatat tgcagcacac    1560
agcgatcgat ataatacaag cgatctgcca ctaccaaaac tttacggttc tgcaaccgcg    1620
tcagcaacgc atgaaaaaga taaacatgct catgcgggtt caaagctaaa atcagcccgg    1680
cgtccggcat atcggataga gaatgcaaaa gtgcggttaa tgagttacac gttttaacgc    1740
acttttccgg atattttttgc ttaaaaatag actgaagggc ataacaatta gtccagttaa    1800
taccgtatat aattacattt ctcatttatt tatccttttt tgaaaactga ccacagcttc    1860
ggtaatgatt tttcttcctg ggcgactact gcgcaagtag ataacgcctt cttactacaa    1920
aggtaataag accagatacg ttattacatg cgcaatgtcg ttaccgaaat gaattccttt    1980
tacaaatctg ataatgatta aatttactgt tttactttac tgtaatctct tagagtacaa    2040
cgattgcccg gcgcctggtg gccatgtatg tctgacaatg aacgctttcg attcccttttc    2100 attaactaca tatcactggt gtagcgatac tgaaatatac actacgatta aaaaatatt    2160 tggtatctgt aacgcaaaca gatagtaacg tttaaaataa tttcacaaat caatggttca    2220
tcgtacgcat aaagctaagc ggtgtaatct taaaatgccg tttaaaaata gcgataaaat    2280
aagaaggcgt atcatagcca cacatcgtcg cgacttgtga atatttcca gcccccatac    2340 gtaataattt tatagcctga ttcatacgag catctaggta tattttgcta aaactcacct    2400
cttcagcggc cagttttcgc ttcagacttg atacgctcat aaacagcttt cccgccacct    2460
cagcctgtga ccatttgcgg gtgagatcgc tgataataat gttataaact ttctcttttg    2520
tcgtaatttt tattgctcgc tcaaggaaat caaacccacc gggcttacgt acaaatgccg    2580
atataagata catcaatgag aaatatgaat aatcatgatc atcaatactc acattactac    2640
aaacccgtgg acatgccaca ccatgcaaaa tagagtcaaa agtatcactc atccctggca    2700
acaagtccgc atgaaaaaaa tactttggtt tcgttttttaa tgatagctct cgatcattat    2760
agtttcttgt actgtaaaaa actttgtaga attttttgcat taagtcatag gaaacttcca    2820
gtgaagaaaa atcaatatgc ccttctattt cgctcatact aagcgtgatt gtttgatctt    2880
tttccaataa aaataaacac ggcgcagatt gttcgatgaa ctccccaaat tcgttttcaa    2940
ttcgcaaact gcctttatta agtttaaaca ataagcagtt tgcgacataa tagtctctta    3000
cgtcagctaa tccatttatt aatggaaatt tgttcggctg ttgaaggtga ttattgctaa    3060
tggcctcaac tgatttattc attgaaggca ataccatatt ttatcctgtg tgctataagg    3120
aactcaaaat cgttatattc ttataaacaa ataattaaaa ctcacagaga tgatttaaat    3180
ccgatttttt tattattata gccaataatt acattccaac gcgcgttcat ttcgtcacaa    3240
aaagatcccc ttacaaactt tatgcacaat tttgtaatga aagcttacaa tattaatata    3300
atcatttcag aataaaacgg ctggcagaca tcttaataat ccatatacat caataagata    3360
```

```
gacacactgg catggtgcat tttctgcatt atttgctgat atatacacca taccttatca    3420
caaatcgcca gcaatggggg ttcaccagtc aattgcctct ttgttttccc cgcccgataa    3480
aataatctcc tgcatccagg aggtcatttg tgactgtgcg ttcattgtac caactaatac    3540 cccgttaaa gcctcatata atgggtgcc cggttcaact tttgctaaca tgttttgtag     3600
catagccgtt tgctgctcaa agaaacaaa agccgaatca ccactgttag gatctttgaa     3660
ggcattcatc tcttgataaa tgctatcttt aagcgtttca gaagaggctg actcaggaag    3720
cgccagaagt cgttggtaga atgcatcata aagatcaacg tcgccgccat tgcttaaagg    3780
cgcgctatcc acattattca gcatagcggc cctggcactc aacgaaacca cacccgtcgc    3840
ttcagtatct gctgtcggga ccaaataaga agtcggaatc gtaccggta tcaccttata    3900 acctccgctt gcgttttgt cttccattca tcaataagtg cgttaatggc gttatcagaa     3960
attgtccggc agtcttgtgg aagttcatca agatgatgct taatgacgcc tactgccgtt    4020
tcaacaaatt gttcaggtga aaattctgcg atctgatcgc cgcaactcat gataaagcgc    4080
tgttcctgat gatatttaag attaaaagtg cctggccagt tctccataag caacaccatc    4140 agttttggt gatctttttt cgcattaact ggcagtgtta aaaaaagttg ccccctcaggc    4200 ttatcgaaat cccttagcca ctcatccagg acggttaaaa gcgtttcggg atggtcgacc    4260
gcagctgaaa ataactcgcg ggcataaatc tgtattttt ccatccactt ccaggccatt     4320
gtctgattat cagtaagata agcggcgacc tgctgtaacg cgtctatcat tccctgctcg    4380
taaccttcct gataggcgta catccgcaag gtctttgcct cttcttccgc ctctcgcaaa    4440
atacgcttag cccgttgatg cgcctgctgt tctaatcttt caatagagaa ataacgttcc    4500
agcgttttac gctttatcag tatcccctca acaggcgaaa gcggggacgg tattgggata    4560 ttttttgagca tattgtaagg ccagtagcaa aattgacatt tctacagcat cctgcttcaa    4620
tgcctcctca ataatggag gaaaagcaa aggaaaacgc tgtgctaaag attcaggtaa      4680
aaattcattt agggcattta actgtgcata cccgacgcta agtaaaaacc ggtgattcgg    4740
cgccttattg cagacagata aacttgttcc ctgatgcatt gccaaaaatg cttgcgccca    4800
atccggcagg ccaagcaagg ctccctgcct tgccagatcg gctctcagtt tatggcaacc    4860
gagtaaatac gctacctgcg gcagtcggcg ccactgacgc agccacagct gcgtcagtga    4920
gttttgaata cactccttttt ctccgttctt aagccgccat gccgccagta ttaactcatt    4980
tgccgccgcc ctggcggcgg gtctgacaat catttccggc gctatctgca accgctgagg    5040
atggatatac gataacggat caaaaatgat tctttgccag ataatgggta atggctgcct    5100
attcatttga cgatttcgcc ttatcatcag ccgttatgcc tttcttattg cgggcataat    5160 ggttttgta ataccagacg ccaaagcctg ctgacatcac ggataacaaa ataatcaaca     5220
caatccaact ggttgcaaaa gaattacgtt ttactggtgt gccgggagcc tgtaattggg    5280
catcagaacg ttctgacaac acaacagaaa tgttgtcata atccacatcg gcaaaactat    5340
tctttaagaa acgcttgata tcgctgatct gatgcgcaag cggcgaacct cgttcatata    5400
cggctaatgc cgacagatga acaggttttg gcggacggcc atttcacca gcatcaatat     5460 cataactaat atggaccctg gcggagagca cgccctccat cgtctgtaat gactgttcca    5520
gtcgctgttc aatagccgaa tataacctgg ccttttcagc tcgcggagac gataccagcg    5580
aatccgccgg gaacatctgc gctatttcca cccgtggccg gggaggaagc tgataagttt    5640
taatccagta caccgcagcg gtaaaatcag gctcagcaac ggtaatgcta tagcccaatt    5700
ttccgctatc aattttattc gcctctatat tgtgcatttg cagaacggca atgacctcat    5760
```

```
tagcctgttc ctggtccagt cctttaaaa gatccttatc cttacagccg gcaagggtca   5820
ttaccagcag aaaggtatat agatatcgac gaatcatgag cgtaatagcg tttcaacagc   5880
cccgactcct ttacgagtaa gggtacttac catagaaaca tacaggttat aatctgaaat   5940
catctcttgc gaaatagcca gctctttagg atccgtcacc agattagggt cctcaatcct   6000
gttggtaatc gtctgtttat ccacagccgt ggcaatcgcc gaaccagaaa aagcctggag   6060
tagccggtca tccagcgaga caatgtccgt ctccatagac ctgatattga ccgcctgccc   6120
tataacggca ttctctggga caatagttgc aatcgacata atccacctta taactgatta   6180
acggaagttc tgaataatgg cagcatcaat atccttaaag acttttaccg tgttcgattg   6240
cgcgttacgg tacaagttat attccgagag cttactctga tacgccgcca gtagcgccgg   6300
atcggagggt tttgctgcta atttatccag cgcctctgtt acctgcgttt gtagattatc   6360
aacgcccgta tcaaattttg ctgagacgtc atccagatag cctgaccaag gtgttgccat   6420
aatgacttcc ttatttacgt taaattaaag tgggcttggg aaataccaat ggcctgggct   6480
cattttgata taaccttccg ccccgtactg aaatgagcgc cccttgagcc agtcatcttt   6540
taattcgatc gcaaactgca catagcgtcc tccccatgtg cggtaatagc tatcgacaaa   6600
ttgacgggct ctgagtattt ctacatcatc gagcgccccc tgaataacaa acgttacgcc   6660
cccctttatga ttcctgcggg aataaggtaa cgcctgctgt tttagcccg cttccgcctg   6720
gcctgctgcg gtaacatcgt ccatcaacgt gatgttaacc gaatccgcgt aaggcattag   6780
cgctctcagc ttttgactta acatctcgag ctctttcttg ctcatcgtgt ttcgctggcg   6840
gcttagccag aaaacgggtt tacgcggctc atcgaaatga atccgataat aagccagctg   6900
cggataatag gtatccagcc agatagagat acgcttattt tcttcgtttt cgttaatcac   6960
tcgcgcattt ttatcataat cgcccctcgc taaaacctga cgagcccaca gcgtatctct   7020
ttcattttgc gcagcgacat agagcatttt gtcccggcct ggcaacacct gaaaacgctc   7080
cttctcctgc cccaataacg aatcgagctc tgcggcctgc cgctgcggcg agttaagtat   7140
ccataacgtc cccacagtcc caattcccaa tataaaaaac ccggccagtg ctgctacaat   7200
tccgttttta aaacgcggct cgttcttttt tgcagacgtt tctaacttct caggctgctc   7260
gggcacccac ggctcgcttt ccgggcgaat caggataagc aattcaccga cctgtattgg   7320
cgtatttaat tgcaccgaac gagattcaga atttccttct ttcagctcat ggagtataat   7380
ttcggtcgta tccgtatcca cctggatttc aaaatttact ccgccatggt ccagcgggat   7440
aaaaaagcta tcggcaggta tatcagggag ttggcctgaa gcagtgagcg catcactctg   7500
acctaccaca aagagtgttc ggcctgtcag caatggaaac tcacagccgt tcagtgagct   7560
gttaagtaat cgaactatgt atggcccagg gcttgttatc gtcttctctt ttgatgtttc   7620
catatatact gttagcgatg tctgtcgttc tcgatagcag cagattaccg cacaggacac   7680
agggattcct gatgaaaata gaatgaaaag tgagaaataa aatcaattta ttctgtataa   7740
tgcgtctcaa cacatattaa agaaccatc atccccattg gggcttaaac tactgtagat   7800
aaattaccca aatttgggtt cttttggtgt aacaatcaga ccattgccaa cacacgctaa   7860
taaagagcat ttacaactca gatttttca gtaggatacc agtaaggaac attaaaataa   7920
catcaacaaa gggataatat ggaaatgta acctttgtaa gtaatagtca tcagcgtcct   7980
gccgcagata acttacagaa attaaaatca cttttgacaa atacccggca gcaaattaaa   8040
agtcagactc agcaggttac catcaaaaat ctttatgtaa gcagtttcac tttagtttgc   8100
tttcggagcg gtaaactgac gattagcaat aatcacgata cgatttactg tgacgaacct   8160
```

```
gggatgttgg tgctcaaaaa agagcaggta gttaacgtga cgcttgaaga ggtcaatggc    8220
cacatggatt tcgatatact cgagataccg acgcaacgac ttggtgctct ctatgcactt    8280
atcccaaacg agcagcaaac caaaatggcg gtacccacag agaaagcgca gaaaatcttc    8340
tatacgcctg actttcctgc cagaagagag gtatttgaac atctgaaaac ggcgttctcc    8400
tgtacgaagg atacaagcaa aggttgcagt aactgtaaca acaaaagttg tattgaaaat    8460
gaagagttaa ttccttattt tctgctgttc ctgcttactg cttttctccg actcccggag    8520
agttatgaga tcatccttag ctcggctcag ataacgttaa aggagcgcgt ttacaacatt    8580
atatcttcgt cacccagtag acagtggaag cttacggatg ttgccgatca tatatttatg    8640
agtacgtcaa cgctcaaacg gaaacttgca gaagaaggta ccagctttag cgacatctac    8700
ttatcggcaa gaatgaatca ggcagcaaaa cttttacgca taggcaacca taatgttaat    8760
gctgtagcat aaaatgtgg ttatgatagc acgtcctact tcattcaatg tttcaaaaaa    8820 tatttttaaaa ctacgccatc gacattcata aaaatggcga accattaaca tttttttgtat    8880 ctgtcactta agtaaagatt tttattaaaa ttgtaataat ttaaaattca gactgcgcat    8940
taacacgctc tatcaggatg ggaggctatt caatatcatt gttctgtccg gaagacagct    9000
tatactgata tctctggtaa tttaaagtaa ggctgattat ataacacgat ttttgtgaac    9060
ttgtcatcgc tatgatgact ggtaaaacga tattgcctta ttcacagcgt aagaattcgt    9120
ccagatgaca ctatctcctt ccggctttaa ccctgtggat taaggccggc attttattca    9180
tatttataca tcatccgttc cctctgagaa ctatttgcct gaacggttta taccgaaaca    9240
gtcacgcttg ttagctttct gccaggcata cctcctctct tcctcctgat atcgatataa    9300
tgcctggggc cagcctgagg atgatactgc tcataaaccc cctgcctttt tgacgctata    9360
actgaaggga gtaagaaaaa gacgatatca ttattttgca aaaaaatata aaaataagcg    9420
caccattaaa aacagtcttt catttatatt ttggaaccta agacaaatta cactcttaaa    9480 cttttcaacga atggtcattt agtggaaatc ttcgagaaaa atggttctga tggtgtaatt    9540
atcagaccat taaccatgaa gatataataa gcagcattta cacccaaaa aaatgcagta    9600 agatagctac aaaactaatc tctattgcaa tgaggccaag ttaaatatgt aaatatttag    9660
atgccaggcg ctgactctct ctgcaccagg atatacggca gcgtccattc gataatcacg    9720
gttagttata acaatattat taccaacatg tcagttattt aaagcacagg cataagctaa    9780
ataatcaaat gttaaaaaca tataaacccg agcccgtaga atatgacatt aagctcataa    9840
taaaagctca acctgaccgt tagtactaac agcagaatta ctgaaacagt agattctatc    9900
ctaacgactt gtattagtta ttataacttt tcaccctgta agagaataca ctattatcat    9960
gccacatttt aatcctgttc ctgtatcgaa taaaaaattc gtctttgatg atttcatact   10020
caacatggac ggctccctgc tacgctcaga aaagaaagtc aatattccgc caaaagaata   10080
tgccgttctg gtcatcctgc tcgaagccgc cggcgagatt gtgagtaaaa acaccttact   10140
ggaccaggta tggggcgacg cggaagttaa cgaagaatct cttacccgct gtatttatgc   10200
cttacgacgt attctgtcgg aagataaaga gcatcgttac attgaaacac tgtacggaca   10260
gggctatcgg tttaatcgtc cggtcgtagt ggtgtctccg ccagcgccgc aacctacgac   10320
tcatacattg gcgatacttc cttttcagat gcaggatcag gttcaatccg agagtctgca   10380
ttactctatc gtgaagggat tatcgcagta tgcgcccttt ggcctgagcg tgctgccggt   10440
gaccattacg aagaactgcc gcagtgttaa ggatattctt gagctcatgg atcaattacg   10500
ccccgattat tatatctccg ggcagatgat acccgatggt aatgataata ttgtacagat   10560
```

```
tgagatagtt cgggttaaag gttatcacct gctgcaccag gaaagcatta agttgataga    10620
acaccaaccc gcttctctct tgcaaaacaa aattgcgaat cttttgctca gatgtattcc    10680
cggacttcgc tgggacacaa agcagattag cgagctaaat tcgattgaca gtactatggt    10740
ttacttacgc ggtaagcatg agttaaatca atacaccccc tatagcttac agcaagcgct    10800
taaattgctg actcaatgcg ttaacatgtc gccaaacagc attgcgcctt actgtgcgct    10860
ggcagaatgc tacctcagca tggcgcaaat ggggattttt gataaacaaa acgctatgat    10920
caaagctaaa gaacatgcga ttaaggcgac agagctggac cacaataatc cacaagcttt    10980
aggattactg gggctaatta atacgattca ctcagaatac atcgtcggga gtttgctatt    11040
caaacaagct aacttacttt cgcccatttc tgcagatatt aaatattatt atggctggaa    11100
tcttttcatg gctggtcagt tggaggaggc cttacaaacg attaacgagt gtttaaaatt    11160
ggacccaacg cgcgcagccg cagggatcac taagctgtgg attacctatt atcataccgg    11220
tattgatgat gctatacgtt taggcgatga attacgctca caacacctgc aggataatcc    11280
aatattatta gtatgcagg ttatgtttct tcgcttaaa ggtaaacatg aactggcacg    11340
aaaattaact aaagaaatat ccacgcagga ataacagga cttattgctg ttaatcttct    11400
ttacgctgaa tattgtcaga atagtgagcg tgccttaccg acgataagag aatttctgga    11460
aagtgaacag cgtatagata taatccgg attattaccg ttagtgctgg ttgcccacgg    11520
cgaagctatt gccgagaaaa tgtggaataa atttaaaaac gaagacaata tttggttcaa    11580
aagatggaaa caggatcccc gcttgattaa attacggtaa aatctgagag aggagatatg    11640
cattattttt ttatcatcgt aatctggttg cttagcataa atacggcatg gctgattgc    11700 tggcttcagg ctgaaaaaat gttcaatatt gaatccgaac tactttacgc tatcgcccag    11760
caggaatcgg cgatgaaacc tggcgccatt ggtcataacc gagatggttc aaccgatctt    11820
ggcctgatgc aaattaacag cttccatatg aaaaggctga aaaaaatggg gattagtgaa    11880
aaacagttgt tacaggaccc ctgcatttct gtcattgtgg gcgcttccat tttatcagat    11940
atgatgaaaa tctacggtta tagctgggag gccgttggcg cttataatgc cgggacgtcg    12000
ccgaaacgat cggatataag gaaacgttat gctaaaaaaa tttgggagaa ttacagaaaa    12060
ttaaaaggaa tgtcagcaga agagaaaaac aaaagacttt ctatcgcgtc aaacaaataa    12120
ttatacagaa atagcttact ttcagatagt tctaaaagta agctatgttt ttatcagcgt    12180
gccgtcgtca taagcaactg gcttgcatt gcttttagtt gtacaaactg tgaggcgtct    12240
tccagcattc tattgttccg tgaattccgg aaatctgcac gtacctgctc cagattacta    12300
tgaggattat ccttaagtac aagggccgcc gccatcgttc cggttctccc cactccgccc    12360
agacaatgaa tcatcggtaa atgcttatct gatgaactac gccccggcgc gccattttgg    12420
ttactatttt tcaccctatc cgccaggtat tctaactgat ccgtagacgg taacggctgg    12480
tgatctggcc aattttcac atgcaatacc gggattgtat accgcttttc cccgcaggac    12540
agttgcatat tgtattggtc tatcgcttct ccctgactgg ctgagctcac ttttggctg    12600 ttggtatgca cctcgccaaa ggtgtagctc cctctgaaat agggtggtaa ttgttttgcc    12660
tgcatctgat cttccgacgt taacaccacc aggcatgagc attctttttc aagaagcatt    12720
ttcatatgcg ctgccagcgc atccggcgta tttttgggt acgaaccggc taatgccaca    12780
ggcttaccgt caaaagttaa cgtattcact ggcacaggca ttccatcgct cagtttcacc    12840
tgggtttgct gattaattgg aatgctgctg accgcaaacc gtgccaggcc cagtgtcggt    12900
ccgctcatcg tctgtggcat tggcgcgccg gcttctattt tctcaagttc agctgtaaca    12960
```

```
tttttcagtt ctttagcaat aacgtgaatt tttttttacag cctgggttaa ttcatgagta    13020
gaggctttat caacccacct ctcaacctct cctccacagg ttccccattg tgagaaccgg    13080
gctacaccga cctgaatatt tgttaacgtt gtaacataat cattaagttg tttagcctct    13140
ggaattttat ttaaattctg taaattcgtc attaatgaac gcagcgggcc gttacctgaa    13200
gccatctcct ggaagttttc tcgcaggcta tttccatcca tttgttccag ttgcggtaat    13260
gttcttttaa gtccctttag cgcgatatcg agtaaaggtt gcttactttc tgctccaaca    13320
tcgttatttt tttctgccac ttttgtatcg ccgcctttta tgactaaagc ggcattcctg    13380
acaccaacat tatccttgct cttaataagg tttataaacc cttcgtcagc agcttttaca    13440
cactccgtga tctgcactgc taaacgttgg gtaaggggtt tgttcatatt tatacgggac    13500
attaacagtg cgtcattaac cgctgtttcc ccatattttt ccgttagtgc atggagaaat    13560
gtctgtaaaa tcttttggtc ctgtactctg atattttccg tatgttttgg caccacttca    13620
gtgttttaa ataacggcat ttttccaagc caggttaata cttttgacga aaattttca    13680
ggcgcaacat atgccttatc agtattttcc ttagcaatat aaagtcgggc atcattcgac    13740
acaccaactt ttgaaaacga agacaacgtt aaattattca attttctctc ctcatacttt    13800
agcatattcc tgcagtatgt ttttgagcgc ttcctgctga ttcacaaatg actcaagctg    13860
cgatataata tggtaagtat ttgtcagatc ggtaattgca tgtataagca acaacgtctc    13920
tgcggcatca atatacgcta acgtaccttc attattcgca gccagttcac cattaatcac    13980
cataatctgc cgccagatag aatcgccaca acaggcgat aacggtataa tcataccgtt    14040
caataaccag atatcatctt tagcttcaat agacgtaaaa atatcgctat cgagtaataa    14100
taagcactga ttgttgtcgt caaaagtgag cggtaaaccc aatttctcac caatattagc    14160
gataatatcc tggtgtgctt gcaatttact ttcctcttga attatatctt ttataagatt    14220
gcttcttcaa atttaatctg gttacacaat gtcttgatac ttttttcgcgc ccatcgccgg    14280
gcgcaatatt tctctccttt aatccagtag aatagccatt cactacgcat cggaacacat    14340
atcagcagct ccttcggatc attttcaaca tgacgtaact tgcctttaat aacaaaacgc    14400
gaactgtcag caatatcatc atatattgca gccatacctg aaccgggtac tacatgtgtg    14460
atgattttca taacaattaa tcttattcaa ttgttgtcaa gcgagagaaa atactacac    14520
cctggactca agactttttt taacaacacg gcatatatcc gcaaaggtcg tcatatcagg    14580
aagatcgttt tcattgcaac taatgtcaaa ctcctcacta agaccaaaata caatatcaat    14640
taaatccaat gagtcagcgt aaagatcctc aaccagattg gtctgaccat tgatactatc    14700
aacatcaacg gcaatacagg aggtgatcac tttttttgact cttgcttcaa tatccatatt    14760
catcgcatct ttcccggtta attaacgctg catgtgcaag ccatcaacgg tagtaataac    14820
ccgatccacg ccaggtttat tcaggtatga ctcgtaagcc gggccagctc gccagctacc    14880
gtctccgata aggccgtcca gcacattact taacacatag tcagtttccc cttttagcct    14940
ggtcagcccc gcctctctgg caaactgcag tgcaatctca gccagttttt cttttgtgg    15000
atgatgagta atgacctctt tgagagtctc cattttcgct ttcaattctg ggtgcttgtc    15060
aatatcgcta cattgcgctt tcaacgctgc actctttatc gtgtcattgg gtaatatttc    15120
cgcacgcaag ccgtcaaacg ctctgcgtac agggaacggt gtggaggtat ctggctccag    15180
ggctttacgt atcacaccca aaaacgtctc acgggcgtcg aaatgcattg aatgcatatt    15240
cgtaacgctc ggtactgttg agaggaaact attttgctta aacttcaaac cagaaaatgg    15300
gccagtctta tctgtctgac tattatcatt atcggtcgta ccggctttat tacctgtaat    15360
```

```
taccgtcgtg tctgattgta aggtatcggt tttaacattc tcgacgccag ccagttgact   15420
ggcaagcggc ttcacattca caatctctgc cgtctggctt tgctgtttat tatcatcaac   15480
gccgtgcacc gtggcctgta ccggcttgcc gataatgctc ttgctggtta cgccatcgac   15540
ttcatcaaaa gaggttgttt cacccatagt gcccttttct gacgtgacca cctttccatc   15600
tttactttcg gatgaagcgt tggtcacagc ctctgccgtc gcatgagccg tgacgtcaat   15660
tttacccgcg atgccatggt caattgcccc tgtgctggcg ctgtgtgccg tctccgtttg   15720
atgcatagtc gaatccacac gcgaatgact atgacttacg ttgctgctgt tagtcgaatg   15780
gtgtgactcg ccattgcgtt ggctgttatc aataaatgtt cggctattat caatcgtctt   15840
ccggctatta tcatggttgc tattatcgat atggcgctgg ctattatcga catggcttcg   15900
gctattgtta atatgcttac tgttatccac gctatggtta ctgctatcaa tattaatatt   15960
gatattaata cccgtaggtt ctgcttttt cccaccatca ggtactggtc cagccgcagg   16020
ctccggaatt ttagggtcag gcagtttatc tgcaggaatt tttgcaaaaa cattacgtag   16080
cagcaggggt atcaacgttt gcatttcaag gtgccgggct tcccgtccta cgctggtacc   16140
ctgctcttgc gttaattttt ggtggcacat atcaagcgcc tcaaccgcct tcgccgccgc   16200
tttgtcaaca aggtgcgtaa gattgctgcg ggttaacgga tctaacgtac agccaaagtt   16260
atgttcaatg cagctggcaa tagggcat cacctcctgc ataacaagat tcgtcgataa   16320
tttacttaat tcaccaccag tgttattttt gataatatct aacagctgct tttccaggtt   16380
ttccagcttc gcttccgctt tctttgtttc tggcagccat ggcccaaaag ctgacttttc   16440
tttcaggcca tcttttatga tttgctcggt atactctgcc cccaccttca tcagtagcgt   16500
cttcgcctca ggagaatcac tggtggcgtt gagcgctgaa cgaaagagcc cggcaaactc   16560
cattatcgct ttcttaccgg cgacattatt tgaattggta aaaacttctt ttaacgcctc   16620
agcgtctttc ccgcatttaa acaatgcatc cagactcgcc tgtttgatca gcgcgggaaa   16680
atcttccagt tgcgggcctt taatttcccc tgacagcgtc gttgtggcac tttctctgac   16740
tgcggaaaga ttcgccgcaa gattcgtggc ctgcgttttg atctcggtct gcatacctgg   16800
tattatgacg gggggctgag tccttacact tgtaaccatt attaatatcc tcttctgtta   16860
tccttgcagg aagcttttgg cggttttcag gctgctactt atcgtactgc tcagcacttt   16920
taccaggttg tcgtacaatg aattggcatt gctatatttt tgcgtcagcg tctgtaatgt   16980
ggttttcata ttttcttcct gcgctttaaa acccgactgc caggcttgat atttggcgtt   17040
atccatttcg agttttgagt cttttcccgg cgcgcctaaa ccatcaatat cctgaaccat   17100
tttttgtaat ggcgtcagat caacggtgac gacataaccg gatccataag atttcaggca   17160
gctattcggt aaattcaatt cactgagcca ctgtctcgct tccgcttcag tggctacttt   17220
aacgccgctg cctgactgag ctggaaataa aacggtatta ctgtttattt gattatattt   17280
attgactaaa ctgtttaaat cattttttgag tgaggtaaca tctagcttaa cggtattacc   17340
gtccttacct ggtaataacc agcctcccat tttggaaaga atatcactga aggcctgata   17400
aaaatcggta tagactgcga caacgttttc ataaacgccc agatagctgt cacctatcgc   17460
cgatatattt tgggaaacca tatcccaaat ctcagcatca gaatggttg ttctcggctg   17520 cgccataggc gaagcgctaa ataaggccga cgtcggcgca gaaaacgcgc tccgcaggtt   17580
ctcattttgt tctgcggata atgacacgcc agacttcgcc agagcattca ggctgctggt   17640
caactgctgg cgcgccagcg tgcgctcgtc attattctct tcagagatcg gtggcgttga   17700
ctgcagcgtc tgctgtgcct gctggatttt agtagccgcc tgcgataatg aaatgatatc   17760
```

```
tgtaccgcga tgttctgtgg tagacggtac cacggcagtc tcgacgtgct cgctcgccga    17820
gggagtctgc ggccgttcgg caacgatccc cggatgagga gaagcggaat aattttgaat    17880
attaagcata atatcccag ttcgccatca ggagcgcgat taaatcacac ccatgatggc    17940
gtatagatga cctttcagat taagcgcgaa tattgcctgc gatagcagca agtgcggatg    18000
ctttcgactg gttaatgctc tccattgttt tcagcatttc ctgaatcagg ctggtcgatt    18060
tacgtgaact ttcacgggct tcgtccgatg cggtgctggc aacacggtta ttcacctggc    18120
taatttgctg ctcggaacgt tcctgagtag cggcgtactg cccggacgcc cctgcaatac    18180
caccgaccgt gaccgagttc ttcataatca gatcgcccgt catctgcatc ttgcgcgcat    18240
caattcgggt catatccatg gtattctgct caagacgaat atcggattcg acagactcaa    18300
gacgtttcga cagaatagcc tgatgttcag gggagatttg tttattactg tctttaatac    18360
ccagactttc cgtggcgctg gttccggcat tagatttaag cgtcgcatca ttaagatttt    18420
ttgtcgcatc ggtaccggtt ttcttcatat ttaacgattt cagagaatcg acgccttcag    18480
caccgagttt gacgctattc tgcccgttca gcacgttttt aatactgtgg ctttcagtgg    18540
tcagtttatc gatcttcgcg gcattatgtt taagcgcgcc tctttcattc tgcagcccct    18600
tatattccag tttggcgccc acgccagtga tccccaactg aagcgcgctc tgggaaatac    18660
taccggacaa cgcattcatc ccttcgcgca tcatggagct tgctgtcgtt ttagctgcat    18720
caaagctgac taatgacaac ttaccagaca gtttgctatc agcctggttc aacgtcagca    18780
ttaacgtatt cgcggcagcc aacagcgcaa cggcactgga agacattccg ctaatatcaa    18840
aaaactttcc gacttctgcc tgctgctcgc gtaactgggt ttgcacaacc tcattcgctt    18900
tagtcgtgac attatttgcc agagcattca aatcctgatt catgtcggta ttttgaatac    18960
tggcttttaa aaaggacgtg atcgttccgg gggtttgcgt taatacccct ggcgcaggcg    19020
cgctcagtgt aggactcaac cccaggtcac tgactttact gctgctaata ccaatactat    19080
tcagaatatc tttagcgcta acggattgcg aagctgtctg tgaactattc tcaacagaat    19140
gattatttaa ataagcggcg ggatttattc ccacattact aattaacata ttttctccc    19200 tttattttgg cagtttttat gcgcgactct ggcgcagaat aaaacgcgaa gcatccgcat    19260
tttgctgtac cgcagaagac atggcttttt gcagttccgc cgttaccttc tggttttcac    19320
caaatatttc tacggattgt ttaagccact gctgaatctg atccatggca aaacgggcga    19380
gcataaaatc agcaagcgcc tcgctggcat ttttaataaa tacgccctcg caacaccac    19440 cggctgactg ggctgcggta ttcgtgactt ccatgcccaa cgccacttta tttagggtat    19500
tacctaccag ctcttactt aaggcattcg tttgcaggcc catcttgcta cctacattac    19560
ccagaccgct agtaatacgt tgcatcccct gggtaaagag tttgctgccg ttttgcgcca    19620
actgtttcag cacgttaggc accaacttct taatcgtttc gcccatcatt ttgctcagcg    19680
cgttacccag tttcgccgcc gcgccttttcc cgacaactgc gaccaccaca atgaccgcca    19740
ccatggcaat agcggcgaca atcgcaccaa caatgctgcc ggccatctct gccgttttct    19800
tatcgatgcc taatccttcc agcgctttgg taatcgcctt gccaatcagc tccattaacg    19860
gcttcagcac atgctccata atcgggttta gcgcctgctg aataaacgac accccgtcg    19920 ccgccttcac aatttcatcg gccaccatta ccgcaagtcc caccgcagcc agcgccgac    19980 tcgccccacc ggtaaaaaca gcggccacaa cgctgacaat ggttagcagc gcgccgagga    20040 cttttcccgat acatcccata atgcggttcg tttcctcggc tttgcgcgtc tcttcctgga    20100
attcagccga tttctttttcc atctccgcct gacgcccttc ctgcaaggcg ttgaaaagcg    20160
```

```
caagatcgtt ttgcaggctt tcttccgtat ttttgcccac aatctcaata aacatggcca    20220
tgagcatagt gaggcgggcg acatttgaca gattatcctg ctcaccctgg gaaacctgat    20280
tctgagaggc ggcattagcc gttccctgga atttggtcag aatgttatcc gctttctcgg    20340
cttccgcttt ggcgtctgtg cctgctttaa ccgtcgcatc cgtggcctta tctaaggcct    20400
ctttcgcctc tgtcgcttct tttccggcct gttctaccgc ggcttcagct tgtgcatagc    20460
cggggtcagc cgggtccagc gattgcaatt tattttgcgc ctgcgtcagt ttttggtcg     20520 cagcgtcata aacactcttg gcggtatccg tcttttttgat actggcttca tagagatccg   20580
tcgcctcctg agcctctccc agagccgtct ggaattcttt cgatacctga atccccatct    20640 cttttttgtga ctcaatcatc gcctgccata ccgccagacg agactccagt tgagacagcg   20700
aaacatcacc cagtagcgtc attaacttgc caagcagtaa tgtcaattgc ccttcgctgg    20760 agagttttttc ccgggcggcg tccgtaggcg gcttcagacc caccgtatta atagcgctct   20820
cgccggactt tgttccggct ttaaggtcgc ccgctttcgt tgccaccaca tctttaaaag    20880
ctttatccgc cgcttttaaa aagtccgtgt tcttacgaac gccttcaaaa gccgcctcag    20940
cgaggcgcgc attttgggta tatccgctac ggctaatgct acttgcgtca tttaccataa    21000
ttattccttt tcttgttcac tgtgctgctc tgtctccgcc gttttttagcg cctccagata   21060 gaccaacgct tttgcccgca gagactcatc ttcagtacgt tcattgacaa gttcaaaaca   21120
ctgtctggct tttgctgcct tacgcattaa taattgacac tgcccggtaa aaaaaacggg   21180
gcgataatca tttttaagta acgtaaacgc tactgcataa aggtcacatg ctttctgaaa   21240 ttgttttttttc agttggcata ccgccgccag tcccatggtg taatcgggat tgtaaaaatc   21300
ataaatgcat aagaaacgaa agaatgtctc agcttcatcc agtcgtccct ggttataaaa   21360
ctcataagca tgagcatata aaccgtccat catatcttga gggatcccat gaacgtcttt   21420
tagcgtggcg ccttcactaa cggcatccca aatcatttcc gcaacacgtt cttcgctgac   21480
attattttga taatccatta cttactcctg ttatctgtca ccgactttgt agaacttaac   21540
gactgcgttt atctgatgca gttattaaac cccgacggtg gttagtgaac attcaaaaaa   21600
cgcccaatga atacatcgct actgctttac gcggctcaat gccgtacctc gttttcttgt    21660
ggctgaataa cgtctttgcc cgcgttttct acctcttcca gccaaaccag aagacgtaaa    21720
acttcatcaa tttcttccag actcaccaga tcataacggc gatgggtttt gaaaagactg    21780
cgcgccagtt tgatatcgac gatcacaggt acgccaacct tctccgcata ggcgcggacg    21840
gccagtgcgc gctgattcgt ttcatacacc gagatcatcg gaatcggcat caattcgggt    21900
ttaaaataaa tcccgatcgt aatatgcgtg gggttggcaa caatcaggcg tgagttttca    21960
atatcagatt tcacctgttc agacagaatt tccatatgaa cttcacgtct tttagattta    22020
acctctgggt tcccttcctg ctccttcatt tcacgcttca cttcttcctt atccatttc    22080 atatctttca tggtcaggaa atattccgca atagcatcca ataataagac aatcaatgcg    22140
caagcaaggc aagttaatac caatgcgagg agaagttcac gccaaatgac ggcaataccT    22200
acaatattgc catttagctg agaaaagatt tcaaccttat atttcttcca gcaaatgatg    22260
gcggccacca caaggatga gagatacagt agggttttga ccgtatcttt aaccgtgcgc    22320
atactaaaaa gttttttttgc cccttctacc gggtttaacg ccgataaatt aggctttaat    22380
gcttctgtcg ccagcacaaa accggcctgt aataacgccg gtaatgcgga acacactaag    22440
cagagcagca taaatggaat cagatatttt aaccctatcc caaaaacggc caaactgtag    22500
tcagccatgc tctgatcaaa attatccgca ataatgatct taattatccc cataaactca    22560
```

```
ttaaatgagc catacgacac cagataggca attcctccca gcgtcaggca ggcgataatg   22620
agatctttac ttttaaatga ctggccttt  ttagcggagt cttccagccg tttttagtc     22680 ggttttctg ttattcga ggacatgcgt cgccctcgc tcgtaaaacc aactgcttaa        22740
ccctgtggcc tggaaagaga gtcgcagtac attgtccggt agtaccggag agaaataaag    22800
cagcataatt aaaacggcaa taccgctttt taccgtcagt gaaatcgcaa aagcgttcat    22860
ttgcggagca aagcgcgaca ataaacccag gaatacttct gacagcaaca gcactaatac   22920
caccggactg gccagaacca aggcgttttg agccacctga ttaataaacg ttaatagcgg    22980
cggtaatgaa ggcgtgcact cgttcatcgg atcgcatagc tgatagcttt tatttaacac   23040
gtcaaccatc gtgaccagac cgccgttttg taaataaacg acagcggcaa acatattcag   23100
gaaattagcc atttccgagg tatcaatacc gtttgccgga tcgatactgc tacttagcgt   23160
tgcccctcgc tggttatcga taatacaacc cagcgcatgc ataacccaaa aaggccatga   23220
tagcagacag cccagcatga cgcctaccgc cgcttcttgc agaactaacg ggatcatcgc   23280
caccgataaa aacggcggcg cctcgttcaa tgcatgcggc catactccca atgccaccag   23340
gatgataatg gcgtttctcg gcgcgccgct taatacccgc ctattcaaaaa acggcaggaa   23400 gaaaaaatc ggcgctacgc gagcaaaccc tagtgccgca gacgcaacca ggtgatgaat    23460
ttcaaagtac aacgcgtaaa gcattttta ccccttagcc aacgccagga atatcacctg    23520
acgcccgtaa gagagtaaaa cttcgccata ccagccagac agtaaaaaca agcataaaca   23580
cacgccaagt aatttaatgc caaaaggcag cgtctgttcc tgtaattgcg ttaccgtctg    23640
gaataaccct accaggaggc cgataatcgt tgcgacaatc gtcggccacc ctgacaggat   23700
caaaacaaga tagagcgcct tattacctgc aaacactaaa tcatccatttt aactatcccg  23760 tctcgtaatg atgtcatgtt gcaatgtcca tatactgtaa tatcaatccc ttagacagta   23820
aggtccagcc atcaagcgcg acaaaaagca ccaacttaat aggtgtagat atcgtcaccg   23880
gactcatcat catcatcccc agcgccagta gcacgctgga taccaccagg tcgacgacaa   23940
caaagggcaa atagagataa aaaccaattt taaacgcgct ttttatttcg ctcagcgcat   24000
aagcaggtaa taacgcaaat attgatggtt tttcaatttc atctttgtca cgctttaccg   24060
tctcggtctc ttctccatac tgacgcttca gttgcgcgtt ttcaaaaaac tgaactaact   24120
cgcgatctga atatttgatc agataatcgc gataaccatc cagaccttca tcaacgtgtt   24180
tacttaatga cgaaatatca ttaaaggtga catcttcgtc ctcaaaatag acgtaggcat   24240
catgcattat tggccacata acaaacatag aaagcagcaa tgcgacgccg ttaagcgtca   24300
tatttgaagg tatctgctgc aatcccaggg cgttacgcac catgacaaat acaatagaaa   24360
atttaacgaa acaggttcct gacgcaataa taaatggcaa cagggtggaa aatgccagta   24420
aggcaattaa tgagatatca ttccccatta ccagactcgc tcagccattc atggatctca   24480
acgcctaagg tgtcattcat ctgtaccagt tcgccattac ccagcaaaac accattcgcc   24540
ataatttcaa cgttaagttc agcattggtc ggcagtgata atagctgttg ctgccccatg   24600
gcttcgagtt cggcgagggt aacgttctta cgatacaaaa caaattccag tttgacgggc   24660
aattgattca agccaggcag agtttctgca gtttcagttg tattattttc ttcttcgata   24720
tgttgaatat ctaacgtttc cacaataatt ccccttcaa cacggttgaa atgacctaac    24780 ttttcgcgt agcaataaac ttccgcacgg gaagtacgaa tcaggagtac atctccgatc    24840
ccgattcggc ccagcaacga acgctgcgta tcactgctac cgattacaaa gcgcaacggc   24900
caacgcagca ttttcggcct gccgcccccg actgcaggca gttcaggaag atattcaaac   24960
```

```
cacaggccgc ccgatcgct cataatgtgc aacaatttcc cttccggcag cgcgcttccc   25020 ggcacgggt tctctacgca taaacgccga caggacaaat gcggcacggg caactcaaac   25080
ggtcgctctg tcgcagcaag ccagggaacg accaggtgct cagcgccagc agaaaccgcc   25140
gcccccgcca gagcgggaga gacatgctca agccagtccc caggttgaat ccacgccgac   25200
caccgttttt ctgcatcgct caaccgaacc cacattcctt gtcgcgtcgg atattccagc   25260
gtagcttcct ggccatggcg ctggcattct gtcgcggttt gcgccaatag ccattcgcga   25320
cgatcaatct gtctcacacg caatgacatc aggcgtcatc ctcctcgcca gattgctgtc   25380
tgtgctgttg ctgctgcgga ttttgttgat cgtctcgcgt caggtgccag cgctggggat   25440
taccgttttg ccattgatca tgcaaacgat gttcaacctg cgtatttgac ggtattaacg   25500
aaaactcccc tgcttgccgc gcctgaatat tgacggaata gtcatttccc cagcgctgaa   25560
aacggtaagt cagcgagcta tcctctcctt tcacgccatc ggcagtcgga aaaatagtca   25620
tcatcggctt tgattgcgcc gctaaaggca ttttttcatc gccgccggtt aattggctaa   25680
gatcggcgat agtggttggt tgcagcggaa gctgagaaac atctttaacc ttttatgat   25740 ctttatcgtc aggcttaccg gtattggctg cggccattcg ggcaggtgcg acatcccgcg   25800
ccagcggcgc gccctcttta cgaacgcctt cgcccgcgat ggctttatta tccccaggca   25860
atgccttgat attatcgtca gagattcccg tggcgttatc ggctacttca ctaacggact   25920
ccacggcttt taaatcagca gataatttt taccgcttac gctttctaac ggcctatttt   25980
tagacgatag caacgctgcg gatttatcta ctttggcctc cgcagaaatc aaaccgacag   26040 attttcagc agtgactttc aacagttttt cagcaatcct gagttcgcct tttccgttat   26100
gatgcagacc agaaacgttg ccattgtgat gttctgattt cgctggcgcg ccatgtcgcc   26160
atgccgccag taataccggt aaagccgttt ctttatgcat tacgaaagca tcgccatagt   26220
cgcgatcttt tttatcaccg gaatattctg tcttatgttt ttccaccgct tttttaatg   26280 cttctgataa accgccaacc tcatcctgct gcggcagtaa aatgttcccg gatgaactga   26340
cagctgacac atcgcccatt aaattatctc ctctgactcg gcctcttcct gctgtatctc   26400
tcgctggata tagaatcttt tctgacggat tatccagcgt tgatagttcc cttctttgcg   26460
caaccaatat ttacttttt tctgaaactc ttcccttttc ttttccagct cgctccgttt   26520
ttcctgaatt tgtataatct ggagttctaa atctttatc tgccggcgaa caatagactg   26580
cttacgtaat aacgtataaa tttcctcacg actgagctgt ctgttttctg cacgcagcgt   26640
atctaataac aatttcagac ccgctatttg ttcaaggatc gcctcctcct cggcctgcag   26700
cccgcggtcc tcatcctgat agcgaagtaa tatcgactca cactgtgaat gaaataccgt   26760
acagcgccgc tgcaatactt taattctggt cagcgaatgc attcataccg ctcaacgtgt   26820
catcaaagga tgaatactgc gctaccggct ggcataacca ggctttcagg ctatcccgca   26880
tctgcatcgc ccgatcgtta tcgatatttt cgccaggacg atattctccc aagtcaatga   26940
aaagctggag ctcttccaaa cgcgtcatta atttacgcac ggcagatgcc tgttcagcat   27000
gtgtcggcgt cgtgacttgt ccaaaaacgc ggcttacgct tttcagtaca tcgattgccg   27060
ggtaatgtcc ctgcccggcc agctttctgc tcagatacag gtgaccgtca aggatagagc   27120
gaatttcatc cgccatcggg tccgcctctt cctcgcttc cagcagtacc gtataaaagg   27180
cagtaatgct tccctcgctg gtcgcccctg ggcgttccag caagcggggc aaattatcga   27240
atacggaggc gggataacct cgacgggccg gacgctctcc cgacgccagt gccacgtctc   27300
gcaaagcacg cgcataacgg gtcatggaat cgataaaaag cacgacccgt tttccctggt   27360
```

```
cgcgaaaata ttccgctacg gttgtcgcca gttgcgccgc attgcagcga tcgaccgagg   27420
ggaaatcgga agtggcaaaa accagcacgc attttctttt cttatgcgaa gcgcgcaaca   27480
tatccacgaa ttcagtgacc tcacggcctc gttcaccgat aagaccgata acaaagacat   27540
ccgcctccgt ttgctcgatc agcatatgca tcagcatggt cttaccgcat cctgcggagg   27600
caaaaatgcc cattcgctgg cctacgccac aggtcaataa cccgtcaatc gcgcgcacac   27660
cggtaatcag cggttcacgg acgccaacgc gtgaagcgta agacggcggt gcgacatcaa   27720
taacgcgttc ttcgctaatc ggcgccactt caggggtaaa acgctcaacg attttccctg   27780
tcggatccaa caccgcgcct aataccgagt atcccaccca cgccgataac gcacgtccag   27840
tgggataaag cacgacatcg cggctcagcc cctgggcatt gccgataagg ctcagcacgg   27900
tgcgttcccg ctgtaagcca accacctgcg cacgtgcaac aacctgtttt tggtgccagc   27960
cacggcgtat ttcacacagt tcgccaatgg ccacatcgcg caattccgcc tcaataattg   28020
ggccggttat tttttgtggg taggccagat attgcagtaa acgaggtgtt ttcatctcat   28080
tagcgaccga ctaaaaactt ccagatagtt gtaaacccca ttcaaggcag tagagaactt   28140
ttcaccgtca gataaaaaat ccggatgcac taaggcttta agcattagct ccccattctg   28200
ctcccccagt agtaattgcc cgccgcgggc aaaatggcat ccttccatga tggtcattaa   28260
gatttcataa gcccgctgtt gtaataccac catgctgtca gcacccaatt gcgcccagat   28320
ccatacatca tcgtccttga cgctgataca gatacttggc aatgcaaata aatccagaac   28380
aattgttgaa tggctatcta ttcctccgat gagtgaagga tcgcaaccac ttacttccag   28440
tgcggaacga actaattcag cgatatccaa atgttgcata gatcttttcc ttaattaagc   28500
ccttatattg tttttataac attcactgac ttgctatctg ctatctcacc gaaagataaa   28560
acctccagat ccggaaaacg accttcaatc attttcttaa taaatcgacg gacatcgaca   28620
gacgtaagga ggacaagatc tttatgtgca atcaataaat catccaactt aagtgtaatg   28680
agatccatca aattagcgga ggcttccggg tcaaggctga ggaaggtact gccagaggtc   28740
tgacggatcc ctttgcgaat aacatcctca acttcagcag ataccattac tgctcgtaat   28800
tcgccgccat tggcgaattt atgacaaata taacgcgcca ttgctccacg aatatgctct   28860
acaaggttaa tgcatctttt ttctcttggc gcccacaatg cgagcgcttc cataattaat   28920
ttcatattac gcacggaaac acgttcgctt aataaacgct gcaaacttc agatatacgt    28980 tgtaccgtgg catgtctgag cacttcttta agtaaatcag gaaatttcgc ttccagttgg   29040
tccagcatat gttttgtttc ctgaataccg aaatattcat tgacgttgcg cgccagcgtc   29100
accgccagac agtggtaaag ctcatcaagc gcgttccgca acacatagcc aagctcccgg   29160
agtttctccc cctcttcatg cgttacccag aaatactgac tgctaccttg ctgatggatt   29220
gttggattaa taccaaagga cacgacttca tcggaataat ttaccactcg catcaaatca   29280
aaatagaccg taaattgttc aacacggatc tcattaatca acaatacgat gctgttatcg   29340
tccaggccct cgccatcgcg taacaatact tccggcaggc gcacgccata atcaataaag   29400
aactgactac gtagacgctc cgcaagttga gcttttttcca gatcttcacg ccggctcttc   29460
ggcacaagta atatcaacgg tacggtctct gtagagactt tatcgagatc gccaatcagt   29520
cccaacgacg ccccttcttt ttcctcaata ctaagcgggct gctcgccttt gctggtttta   29580
ggtttggcgg cgctacgttt tgcttcacgg aatttaaaat agaagagtac gcttaaaacc   29640
accgataaaa taacaaatac cggcagcggg aatcccggca gagttccat tgaaatggtc    29700 aaaatagccg taacaaccaa tacaaatggg ttgttcaaca gctgcgtcat gatattccgc   29760
```

-continued

```
cccatattat cgctatcgcc atttacgcga gtcacgataa aaccggcact aatcgcaatc   29820
aacaatgcgg ggatctgggc gacaagacca tcaccaatgg tcagcatggt ataagtagac   29880
agagcggagg acaaatccat accatggcgg gtcatcccca ccgaaatacc gccaataaag   29940
ttcacaaaga taataatgat gccggcaata gcgtcacctt tgataaactt catcgcaccg   30000
tcaaaggaac cgtaaagctg gctttcccott tccagtacgc ttcgccgttc gcgcgcagca   30060
tccgcatcaa taataccggc cttcaaatcg gcatcaatac tcatctgttt accgggcata   30120
ccatccagag aaaatcgggc cgcgacttcc gcgacgcgtt ctgaacctt ggtaataacg    30180 ataaactgga ccacggtgac aatagagaag acaacaaaac ccaccgccag gctatcgcca   30240
ataacgaatt gcccgaacgt ggcgataatt tcaccggcat cggcttcaat caagataaga   30300
cggctggtac tgatcgataa tgccagacga aagagcgtgg taattaacag taccgcagga   30360
aacgttgaaa aactgaggat tctgtcaatg tagaacgacc ccataaacac caatatcgcc   30420
agtacgatat tcagtgcgat caggaaatca accagatagg taggtaatgg aatgacgaac   30480
atagaaatga tcatcaccat tagtaccaga atcagtaatt caggtcgtaa acgagcactg   30540
ttaagtagag aaagcagcac tataggtatc ctgttaatat taaattaaga cagcttttca   30600
atagtacgac gctgttctgc catttcatgc ttgtaggcaa tatcggtcat actacgtaac   30660
gccattaaca attcttcctg ccaatattct tcataaaaga gtgaagaggg tatggcttta   30720
catacttgat aaaatatctg caaaaggat gcatgttctt tatgactaag caataacgca    30780
ttcaaaccta taatatcggc taacagcgaa tccacttcat gtggctgttg caatagcgaa   30840
agcatcagta gtagccacga cgactcctcc gcattaaacg ctttggtaaa cgaatacgac   30900
aacaatgtac tcacaaacag taggtcagcg gagcgcaaca ttttaagttg cgtcaggcgt   30960
cgtaaaagct ggccaaactc caggcgcgaa caactggcgt cattcgcgtc aatatcggtt   31020
aatagcgaac cctcaataaa atccagtacc accagtcgac gttgatagcc ataactggct   31080
atccagtcag agtaaatctc cacttcatgt gattcactct ggataaattg ccgatagctg   31140
gcgcgcaata agcctggttt taacgataat gttttcccaa aaagccgggc cttcaacgca   31200
caattaatcc ctgccttgag ggtcttcgga tcggtttgct cttcaacgtg cttaagtaac   31260
gactccagct ttttccgcac gatctcttcc aggtctttac gacgaagcaa ttcgcgtaac   31320
acaaggacta aatcactggg gtcaggaaat aagctacgcg cctgacgtaa aaaatcttct   31380
aacgcgccgc catgtacgct aattagcttt aagatttgct tcgccttcgg taaagcctca   31440
tcttccagca cgcgttcaaa actgttagat aaattactgg attttttttc ataatcgcga   31500
cggttacgaa attgcgccag cgccgctgac atttcgtccg tcgactggac aaattttgt    31560 acttccgccc ctggagacga atcctctgcg gcctgttgta tttccgcctg ttgcgcatca   31620
gtatgctggg tcgcatcctg atgagatgtc tgccgggaca atattctgga aaatgaaata   31680
ccggaggttg agccaggaat catttaattg cctcctgacc tctatccaga taaacacgaa   31740
cccatttctg taacttatcg tccccactcc aggcaccgct ttgcttcaga atattgttta   31800
ccgattcgct ggcatccggc gttaacgggt cgacaatttc ttttggttca atcatgaaca   31860
cacgaacaac attactttta ttcttactgg aatagcggaa caggctacca ataagcggta   31920
atttgcctaa aaacgaata ctttggacag tatcggtatt tgcatcccgt gtataaccac    31980
cgaccagcaa actttttccg tgcggcactc tcgcaatagt gctaattaac gttcgcccga   32040
cttcgggtaa cgcatctacg gaggtggtag tatcggattg cggcgtctta tcgttgccat   32100
cttcaatgtc cagcgacatt tctatctgac catctgcgga aaaacggggc agcactcgga   32160
```

```
tcattgttcc gtatgttaca tgctcaagcg ccacattacg ttccccaatc agcttggtgt   32220
aaaacgttct gttgttatca aaaatagcgg gaacattttc ctgggtcagt aataccgggc   32280
gtgaaaccac cgtcgcctgt ttcttctctt ctaacgcatt gaccgcggcg atgaatcgac   32340
tgccatcgag ggtacttatt gaagactggt ttaatgacac gccaagtttg tccccaatag   32400
taatgctgcc gctccatgaa gtgcccaaac gctccagatc gcttttatta agatcgacaa   32460
tccacaggga taattctacg tgacgtttgg cgacatccag cgctttaacc agcatttcga   32520
taaaattcac ctgctcagcc gttcccttta ctaacaaact gttggtatcc ggataggcca   32580 cgatttttaat attgcccgcc gcggcatttt gctttaaagc ttcctgcaga ctcatgccac   32640
cggcataatt tgctgcttta cctttttctc cattcgctga aaacgctggc atcgccgggg   32700
gttcgctact gacaatatta cctaaaggtt gctcttctcc ctgcaacaac ctttcaatgg   32760
ccgtggcaat accggggata accatttttct gatcgcgcag attataggta cgatcgccca   32820
cgaaggtatt gttcagacgc atcacccta ttttctgacg tcccagctca ataccatcgt   32880
tttgcttgtc catcatggtg gcggcgttga ccaccatatc aacatagacg ggtggccctg   32940
aaacatagaa tgttccttta cggttatcgc cacgtagcgg gtaatttttg ttatataaac   33000
ctgagcgttt tagaaaattg ttgaactcat tgagtgagac gttgcgtaaa gaaaccacgg   33060
cattgcgcat ttcactggcg tcataaatat agatagcctg cccatcgaaa taccaaatca   33120
gccccagttg tagggaaagc ttctccagta atgcgttagg atcgtgaaac tcaaagttgc   33180
ccgtaatttt ttttcgtgcc gccatttttgc taacaatgac aggctccttt agctgtagcg   33240
ccatggcatc gaaaaatgtc cgcaggctat cgtctttcgc aacaaaccca cttcccgtta   33300
caggtatttt ttcactagaa taaccaggtg taaccagaac aagcgcggca catgccagca   33360
ctctggccaa aagaatatgt gtcttcattt gtctgccaat tgaataatat ttgataattt   33420
ccgcggcgaa acgccgatca gctctttgat ctcactagaa aaatgtgaag gcgatgagta   33480
accatgatta acggctaatt gggtgatgtt ctcgtggcct tctacactat tcagcagcga   33540
ttgcgccata cgccagtttc gtaattcact cttcgctttt ccgcccaacg ctctgctgca   33600
caaacgacga aaatgggtat aagaaacgcc atagtcttct cccagcattc tcatcgtgtt   33660
gccgctggtt gactgagcga gtaaatagcc aaccaaccag taactctcgc tttttcgtaa   33720
cagagccagt accttattga aggccggaga aggtgtaata atttgctgca aaaaccagta   33780
ctcgcagcgt ttacgatctt gccaaatagc gcgaaactca ggactcagca aacccatttt   33840
atcggattca gcatatgtcg tgtccactaa tcctgcgcca tcgataaatg ccagtaattt   33900
gctgagtact tcaattttta acggtcgaaa aaccaggtct cctgatactg gtgcgacaac   33960
ggcctgctcg caaaaagca gcgcgccttc ctgaatcagg caattttcat tgtgtcggct   34020
ttcagaaaat gacatatgca gcttttgcgc ggaacacgtc tgtataaacc atgcttccgg   34080
gctgcggatt ttccgcttct ctccttcttt aagtacttcc tgcgtattta gcatagttgt   34140
cagcaccagt taaaaatcat tttaatatgt aaacaatacc gggagcgggt ggcaaaatcc   34200
tgatgcaatc attatgaaac tgatgccgcc cgctaattaa attggccaac ttgcacagtg   34260
cttgctgatt taaaatagaa aattagctca tagtgtataa attctggctt attgttctgc   34320
agcagcaaaa attcagatat tgtcatctgg atggagaatt aattatttat atcaggagtt   34380
ttttttgcta gcattcctga aacgcattcg cctcttatca ctattgtcag ataacattct   34440
gacggttgtg taaaaacatt gcgcctcatt ctttctgtagt tggagttaat atgaaaaaat   34500
tttatagctg tcttcctgtc ttttttactga tcggctgtgc ccaggtgccc ctcccttcct   34560
```

```
ccgtgagcaa accggtacag caacctggcg ctcagaaaga gcaactggcc aacgcaaata    34620
gtattgatga gtgtcagtct cttccgtatg tgccgtcaga ccttgcgaag aataaatcat    34680
tatcaaacca gaacgctgat aattccgcat caaaaaatag cgcaatcagc tcaagcattt    34740
tttgcgaaaa atataaacaa accaaagagc aggcgctcac cttcttccag gaacatccac    34800
aatacatgcg ttcgaaagag gatgaagagc aactcatgac cgaatttaaa aaagttcttc    34860
ttgaacccgg aagtaagaat ttaagcatat atcagacgtt acttgctgcc catgaaagac    34920
ttcaagcctt ataa                                                     34934

<210> SEQ ID NO 2
<211> LENGTH: 25262
<212> TYPE: DNA
<213> ORGANISM: Artificial Sequence
<220> FEATURE:
<223> OTHER INFORMATION: Salmonella pathogenicity island-2

<400> SEQUENCE: 2
ttatggtgtt tcggtagaat gcgcataatc tatcttcatc accatacgta acaaggctgc      60
aacgggttca ataacgtttt caggaatttt atctccgcgt tccacttcaa aaataatga     120 gcgggccagc tcaacatttt caacaacggg gatgcagttg cgttcagcga tgttaacaat    180
atagttagct tgagcatcac tgccttttc caggacgcgt ggtattggca tatcggtggg     240
atgatagcca agacaaaccg caatatgcgt tggattacgc actaccgcaa cagattgttt    300
aacagattga gctaaactcc cactttgtat ttcactctgc atttcccgac gccgtgtctt    360
catttgagga tcgccctcca gatctttatg ctcctgtttt acgtcatctt tactcatttt    420
tagatctttt ctaatcttat aatattgaaa agaatagtcc agtatgccaa cgacgatata    480
aaaagccatc accccaaccc ataaccattt tattaaagaa gaaaccacaa gcaggccaca    540
ggctaaccca cagtacggta gcgcccgaaa agtactggca taataataaa agaaaaaagc    600
aaagataaga gatagcatga taactttcag gctggattta cataattcta ctacgctatg    660
taaagagaat atctgcttaa aattacttac cggatttata tgctcgcttt taaaacctat    720
ggccttgctg gcaataacca ccccaccctg aagaaacacg ctaccacag tagcaactat    780 taccccagcg cccagaaaca gcagtgcaga agtcagtgac tctattaaag catgactcaa    840
ttgcgttaat gcataagaaa atggtttatt tactaattgt aatgtgaaag ttattgactc    900
aatcagtatc aaaatcatct tttcagtaaa gaaatgaaaa tacaaataaa gcgcaatcag    960
ctgaaataat gatgttattt caatactttt gacaacctgc ccttccttac ggccatcacg   1020
taatttcttt tctgtaggct gttctgtttt ctcgctcata cagatggaaa ccagtctttt   1080
agataaatat aaaatttatc gctttcaacc aaatagtgat gaagagcata agggaatgag   1140
atcaggagcg tcagtagaac cgatatactt ttgagcggca ttgagaggaa aaacacattc   1200
aattgttgtg ccgaccgatt taaagacct aaagccagat cggctaatac catacatatt   1260
atggcaggaa gagagaagct gatacataat tgataaagcg ttctccactc tgcctggata   1320
tattttaaaa attgctggtc aaataataaa gtacgccctg gtggtaaata ttgatatgac   1380
tcatacagaa tgtttaatat aaactccatg ccgccgctta taagaaaat aacacacaag   1440 aactggctga aaagcaagcc aaaagtgag gtttcagctt ctattgtaga attgaatatc   1500
gtacccattg tcgcgccacg taaagtatca agcagaaacc ccgccatatc aacggcccaa   1560
aagggaaccg ccgcacaaaa cccaattaaa aaaccaataa tcacctctcc ggtgactaac   1620
cctaaccagc tgtaatcttt accaatatgc atcataatct tctgctggta aatgattggt   1680
```

```
aatatgggaa aggtaagtga cataagcacg ccattacgta aaatcgcgga ccctaaactg    1740
ccacttttta ataggggaag taataaagag aggctcaatg gtcgaataaa agccacagcc    1800
aatgcaataa gccactcatt tacctgttgt gccattcaac catgctctcc aactcgtaac    1860
attatctgcc gggtataatt caacaggata ccgctaagcc atgggtagct gaccattaag    1920
gttattgcaa ttgccaataa tttaatcatg aactgtagcg tttggtcctg tatttgagtc    1980
aaggcctgaa caaggcttac gatgacacca actaccgatg ccaccaacac caccggcata    2040
gacgtaaaaa ggacgatcca taaaagttgc gttacaaatt gcgtcaattc agaatcattc    2100
atgaaaagct ctgtaccaat tgcgccagtg tcagatccca accgcctgcc agtaaaaata    2160
ttagcagctt aaacggtaat gaaatggtca ttggcgatac catcatcatc cccatagcca    2220
gcagtatatt tgaaataagc aggtcaatag ccagaaaggg aagataaata agtaatccaa    2280
tccgaaatgc ctgcgtcaac tgactcaccg taaatgccgg aattaatatg agcaaagaat    2340
caggttttat ctttcttttt atgtcttcag gccaggttcg ttttatcaaa ctccgaaaat    2400
aattggcttc cttctcttca gagtttttt gcaaaaactg tcgataaggc gctaatgctt    2460
tactgtccca ctcagacgtc cagaaaggag cgccagcgac ctgaaccgga tgccagcgct    2520
cttttacagc taatagcgtc ggccccataa tgaataagga agtacaagc gcgaggccat    2580 acagtgcgat atttggggga acttgttgaa tacccagagc atttcgtaaa atcgaaaata    2640
ccaccgccag tttaaggaaa gaggttccca tgacgataat gagaggcagt attgaaagca    2700
gaaacaatat accaatcagt tgcaaaggcg aatcgggtaa agacatactg tatctctcat    2760
gacacgacct agaacgctat tatattgttc gcatattatt tttcttatca ggtttacgct    2820 gtattttgc aaagataccaa acgtgtaata cgcaccataa attcattgcc acaggcaatc    2880
aactcacctt gcccaataat acggtcattt actcttatcg tcacctctgg cgcaaaacat    2940
ccacctacag gcaaaacgtc ccccgtttta agttgtcgta attgtccaat ttccagactc    3000
gcacgtccga tctcaaagag cacctgttgt ggtatctgct caagttctac tgaagatgtt    3060
ccgtcactct ttgacattgg actccctgac gcaagtagcg tttcgatatc ctggactaat    3120
tcatcaaatt tcatcgtgtt atcctctgtc agcaacaccc tcgcgtagat cccccaggt    3180 agttgaatag caaaaaaacc gagtctgatg tcgccaaagc aatgaatccg aacgcccatg    3240
ccgatttcga tagactcaag ttcaattaac gtaagctggc accagcctaa atatacaggg    3300
actactacag gaggggcagg ataaatctgt tgtcgcgcag cagaaagctc tccgactata    3360
ttgcgcaaaa aacccgttgg ccatgtaaaa ataatgctat ggaactcatg ttcttcaact    3420
gtccatttaa tatgcaacgc tagctgatgt ggtagattac tgcaggatgt tggcggttcg    3480
ttctgacaga gggttgcatc actggcttgc aataacggcg ccagccccca ttcagctatt    3540
ccatatagca attcaggatc gatagccgat cgattagcgg tgccaattaa cccttcacac    3600
cagcgctgcc agcattcttc tgcaatccac accctaccca gctcattatg ataatttatg    3660
gtaaataatg tcccttgctg tactggatat tgttgcatac tcaatgtcag ctcaccaatg    3720
gtagcgcctt gcgttggaag catctccatc cacggacgct cttcattcgc tattcttaac    3780
atagaatatc tccagggaaa ttatatacc catatgcagc aactgagact ccagccactg    3840
ctttagcgct ttcatcgaac ggtaaatttc atgatgaggg acattgattc ttaactgaat    3900
tagcccccct gattcacaga cttcacactc taccgtcca agataaccgc cactaacacg    3960
ataacgttgc gtaaaaacca cgttcttatt caatgctgca ggaggattat tctcaccaat    4020
gggtaatgcc tggtgcatga gttgttcaaa gtccatacgt tccgcctccg cctcgttatc    4080
```

```
atcctgataa gactggcatg gcaacccaag acttccctca actttggtaa tacgcatcgc    4140
ttaataccat agtaattttt tctttctttt tcataagcgc attaaaattc ttctgtaatt    4200
cgcttcgccg ggagacaagc tgctgatact gattctctaa ctgctgccgt tgcgtcaaaa    4260
agctctgcgc ctgagtgaat aacccggcca tttgttgttt cttatccaac aataaatgac    4320
aagataacgt accttgccag cccattaatt ctttcagtct ggtagacact gctaaagcgc    4380
gcgtctggca atctgctgt tccgtaataa tcgcctgttg ctgctgatca agtacggtaa     4440
gcttgccgcg taattgcttt tcacgccgcg cgattatctc cagcaaagtt tccatgatca    4500
ctcggtgagt atttggtgta attttctat aagtagctcg ggtccgcata cttcatcctt     4560
actttgtcgc aaaatgtgc aaatatccgg ataggtatca atggctttgt cagtatcagt     4620
atcaactcct cgctggtatt ccccaatgcg tattaacagt tcaacctcct ggtaaagcgc    4680
caggcgccgc cgcaatatcg ccgccagttg acgatgctca tggctggtaa cgactggaaa    4740
aacgcggctg agcgttgcca gcacgtcaat ggcaggataa tgcccctct ctgcaagccg     4800
ccgggatagc acaatatgtc catcaagtag tgaacggact tcatccgcca acggctcatt    4860
catatcatcg ccttccacca gtaccgtata aaatgcggta atactgcctt tttcccccat    4920
tcctgtacgt tctaaaagtc gtggcaatgc actaaatacg cctggcggat attctccaga    4980
aactgcggtc tctccggcgg ccagagcgat ttctcgtgcg gccctggcat aacgcgtcag    5040
tgagtcggca agcaagacga ctcgctttcc attatcgcga aaaaattctg ctatcgtggt    5100
agccacaaac agcgccctca cgcgctctaa ggcgggtctg tcagaggttg cgacaacaat    5160
gacacagcgt tttcgggtct cttcagacag tgtaaaatcg atgaattcgc ggacttctcg    5220
tccacgttca ccaattaaca ccagaacatt gctgtctgcg tctggcgcat tacacagcat    5280
cgccagaagc gtgctttccc ccacgccagg agcagaaaaa atacccactc gttgcccttc    5340
gccacaggtt gcaacgctat caatagcgcg aatcccgtc attaatggtt gagtgatagg     5400
ctgtcgaacc attgcgggag gaggcattgc atcatagtct ttccagcaga cgtcgggcag    5460
ttcgcggcca tcaaggggac gaccaaaacc atcaatgact cgccctaata acgcttcgcc    5520
cacgggaacc tgatggcttc gccttaaggc catcacttgc tgcccgcagt gaagtccgat    5580
tgtactcgta aaaggagata gcaaagcttt gctgccatta atccccacga cttcagcaag    5640
ttcttctcca ggctttatac agcacaactc acccataaat accccaggca accacgcatt    5700
taacaacgtt gcgctgacat cctgaattcg gccccatcga caataaccat cgggggggcgg    5760
atatttcagc ctcagacgtt gcatcaattc attcttcatt gtccgccaac tcctcttcgc    5820
taaggtcaat actttctacc acttgtataa ggctctcctc tcctaattcc tgccatgaca    5880
aaatcggtac gtcgaacaag gtggcttctg taattttcg caagaaacgt cgggtgtcga     5940
cagaagtgac aatgaataat ttggctgact gcttcagcgc ctgctcgata agttgcagga    6000
tctgcgtctt atgacgagac gacagcgcag tataggtccc cattaccgtc tggcgaatgg    6060
attcacgcac gaggttctca ataccttcgc cgatccgcaa atcggcagc ggttttcctt     6120
ccggattaag acgacgcaga atatgacggc gaagcgcgat acggacatat tctgtcaaca    6180
tcaggacatc ttttttcacgt ggcgcccagt caattaaggt gccgaaaata agacgtaaat    6240
ctctaataga aacccgttct gatacaagcc gttgcaaagt ttcagcgatt ttattaatgg    6300
gtaactggcg ttgaagctct ttcaccagct cagagtagtt ttttttccatc gcattcatta    6360
gataacgcgt ttcctgaaca ccaataaact ctcccatatg ccgaagcagg acacatttta    6420
ataaggcaga gatacgttgg ctgcccgcga aaacgtccag tccaaaacct tgcgccttat    6480
```

```
gggccatgtc ttttgtaagc caacagatct gccccatccc gttcggtaac gtctggctgt    6540
cacccaccac actagcgtcc gcgcctatca ataaataatc cgcctgagcg ggaatagata    6600
aactaaatac gggttcctga tatagcagta ccgtcaattt ttcggtgggt tcaggcaaaa    6660
cctcaatatt cacctcaggg agagggacgc cggtatcctc aaataaaaac catctcatgg    6720
cgtcaatatc acgaatcagg tcggcagaat gtaacgtcgg gctaagacgt aagattagag    6780
gacatgcgcc gggaaccata ctatcttttt ccggtgcttc gacgccattt gcggaaacca    6840
cagacttttt gcggcgaatg aggataattg gcaatgctaa caacgctgaa agaaagcga    6900 gagtgataaa aggaaagcca ggaattaaag cgaggagcat taaaaccaca gcggttaata    6960
tgagcgactg aggttgtctg gcaatttgag aactcaactc tgtcgccagg ttctggcgtt    7020
tctcacccgg gacacgggtg acaataattc ccgcgctaag ggaaatcagc agcgatggaa    7080
tttgcccaca taaaccatct ccgattgaca gtacgctata agtgtgaaca gcctcactca    7140
tcgacatatc atattgtacg atagcgataa tgataccgcc gataatgttc accagaacaa    7200
caataatacc ggcaatcgta tcgccttta caaatttcat cgcaccgtcc atcgcaccga    7260
gaaagcggct ttcctgctgg acatgctgtc ttaatgtacg ggcatggtct gcatcgataa    7320
ctccggcacg caaatcgcca tcgatactca tttgtttgcc tggcatccca tcaagcgaga    7380
aacgtgcgct aacttccgcc accctctcga tacctttgt aatgacaata aattgcacga    7440
tagtaatgat ggtaaatacg accaacccaa cggtgagatt tcctcctacg acaaacttac    7500
cgaaagcatc cacaatatta ccggcattat gttgtaacag taccagccgt gatgtgctga    7560
ttgtgagtga caaacgatat aatgtagtaa taagtaataa agacggaaat accgataaat    7620
cgagagggtc actaagataa atagcaatta agagcaggat cactgaaaac ataaggttga    7680
tagtaatcag gatatcaacc atccaggtcg gcaaaggtaa cagcatcatc acaatagcga    7740
ttaataacac cgtcgccaga accatatcct gccgacccgc gcatacactg agccactgtt    7800
gcgccctgac tccctcacct aaccatgaac gcattgcgac tccagaaatt ttatttgtcg    7860
atgatgtaat cgtaaccaga gctcggcgga gctggaaaga ggtggagaac aactcattgc    7920
aagcccatcg cgcaacaaaa ataatcgttg aggaataccc tggaacgctg cgggtttcca    7980
gttagccaac gctttaaaaa gcagttcttc gtctaagaag gtttgcttga gtatctgaca    8040
taagtgaata cgacagttat gatagtttag ataggtttca tattgtcctt gccgccagaa    8100
catattggtc gctaaaggcc gttcagctaa tcctgctaat tgaataaaaa gctgaatatt    8160
acgttcagta atgagatccc aatccatcct gacgcctcat gatgagccag aaagccaatt    8220
tacctaaata ttgaaagcca ggtatcagaa taaaacctga tttatcttta cttcacgaag    8280
cgtttcgaga atttgttcac gttgatcttc gtcgttaaaa cagttatcgg gtatcagcat    8340
aaactgcgca tcaagttgtt ggagtaaccg attgaacatc ttcgatgaag aaactatagc    8400
ggtaagtcta tcaagcaacc aatcactgaa aagccagcgc tcacaaataa tatcgagtag    8460
tagcggcagt aatgtattag gcggcaactg gcaaatccac tcctcacgct ggcactcttt    8520
ttcaaggcca aggaataaca gcaaacgacg caaacgtact aatgctgcgg ccaaacgact    8580
ttgctccgag ggttcgatgc atatgctaag ttcaaaggct attgctctta gcaaaatacg    8640
gacccgttca cagcgatccg gccagtctgc cacgcgtctg aaccactgcg ataagggcat    8700
ttcatcgttg tctatcgcct gttgcataaa acgcttcagc gaggacagcg tagcggtatc    8760
cacttcgcca agttccagta aactaaaaac ggcaagttcc catccctcct ccgctgtaag    8820
cgtatccagt tgcgattgca aatcgcgttt tttctttttt gacaacccgc cggcagtaag    8880
```

```
cgccattgca agagcgataa tttgatacgc attctgtaaa tcaggatcac tattctcttc    8940
ggtaagcgga cgcaacgctg ccccattatc ctcctgtatt tgttttatca aacgcagcaa    9000
agcctgctgc ctgcgctcca gtttctcagc atcagtgaat ttattacttt cgcgcagttt    9060
accactcagc gccattccta tttcttccat cgtctcatag agcgctgccc ccgtcgtttc    9120
ctgtaactcc tggagagcta acattgaagg cgaaataacc tcttgttcct ctataacctg    9180
gccaggggta aatgctgtag ggggcgtcat ttttatctca ttaattttaa tattcatcgc    9240
tacctctttt atcttcacca ttacgtaacc atttcagtaa cgcgttgaaa tgacgagaaa    9300
gtgaaaactc aacggcatat cgtgttgagg aaagttcagc ctgatcggga gagaaaccag    9360
gctcgataat caacgtaaac cgcttgccaa aagtttcacg catcaatgcc tcttttttcag   9420 gatgaatacg caaataaagc gctccctctt ccgccatagc cgtggcctgg cgtgccagac    9480
gatggcacat aacactgtct accgactgtt ggtcgaacca ggccaacaga acctgttcta    9540
tactattttt aatatgatgc gctgcgtgat cgaccaatga acgaaattga ttttcatctt    9600
cttgtaaatg ttttacatgc tgttccagcc attccactcc cattttttcc agcgtatttt    9660
tacgcaagca cgctagttct tgttgctgct caactttctg ttcacgctga taacgatagg    9720
cgtctcggat gattttttca gccttacggt aagcggagct cacaatagca tgtgaaactc    9780
tcttagcttg ttgctcttgc gcaaataaag ttaattgtaa tgttatccac tgtgactcaa    9840
taatatttcg agcgggtagc ttatggttaa tttccgtcag aggaagtgaa gtaaaactca    9900
tagcaaatgc tccatgaaga taatctcggt aagagaagtc ttcggccaaa gtatacgctg    9960
cggagggggt aataatacta atagcgcatg taaaaccgca tcgtcatgcg cttcccgatt   10020
aagaatggcg gtaccgatct gcaatgcagt ttgttgcatc acttgcggag gaagtatttt   10080
gccatctctt tgccccaacc aaccatatag ctgccagatc tcatcctcgc taaaccactg   10140
tagaagcaat tgccgatact ctggtagcat aaaatagtca ctacacctga gtttgaataa   10200
tcccagccca aaggcaaatg ccgatatacg cggcgcaaga cgaacctgcc gcttttgcct   10260
gtcatttaaa caggctggaa taacagagct tcctcttagt ctatttaacg ctctgtcaag   10320
aagacgatcc aactcgggcc gatcgccata acgccagcag tttgaaagat gaaagcccag   10380
cttatccagc cattccggta cagcgtaacg agcaggttgc cagaaataac gataaagttg   10440
caacacctcg ggatcaggtc ggctcaaaaa cggcgtctca ggcaaaaata gccgatcagg   10500
atgcccactc ctaataacag tcctgtcaac gataacatca actgataagg gtatttcatc   10560
aaccacttca ccaccttccc tttattggcg ttgataacgt ccataatcca gaatgtttgt   10620
ctcgcgggta cgtcagctac cattctgaat tcagcaggct gcatcaagag actaatctta   10680
ctgtattgca acccagggat tgacatctct attaaatcct taatttttac ccgaaaggcc   10740
tccatattga cctgtggtga atattttata aatacggcaa ctgagctcgg agaagcgtta   10800
cttccctcat cataagtcgg tagcgcaatg gtcactttg cattaatcac gccctccatc    10860
tgactcagca ttccttcaat tctttgttct tttaaaaaat taatcttctg ctgttcttcc   10920
tggggtgata ccactaactg attagccgga acatccttat ccgccgttgt aaactgacga   10980
tgcggataac cgttaagtct aagtagctca accgcattaa taaactgcga ctgctcgaca   11040
cgtaaggtaa caccgtcctc ttcctgtttt ttttccgcat caatatgatg ctgcataagt   11100
aatgccagca tttgattcgc ctcatcctct ggcaatgagc gataaagatc cacatcacat   11160
gccgtaagaa agaacgtaag gacagtaaga aatactatac gatgagcctt catgccatgt   11220
tatccagctt attaagcgct tgcgatgctg cgcctgatat tctggcaaga taatcgacgc   11280
```

```
ctaccgttaa ctgcatataa tccatttgtc tggtcaacat aacctgcggt aataaagcac   11340
tggcgttact ggtggatgct tcatctttca gcaattgttc aaaaaaatta atttgctcct   11400
ggctcggttc tgcagaggac tttacataag attgagtgct tacaggcact acgctcatat   11460
cagaaatatt caattttcaa acccctcatt tggtgcagga ataacagac gcagcgccat    11520 agcctctggc aaatctatat ccgataaaat tttcgcggct tttagcggct catttaaacc   11580
cgccaacaat aatgccagac ataccaactg taattttta tccggaacaa taaccgttag    11640
cgctggtaac atcgcatgta cctgggaaat caggctatgg ttaacgcccg caaacatgat   11700
ttccagcagc aaccgtcgaa catcgtcgct aataacttca gattttagca atgattccac   11760
taagcatatc cttgatcatt ttgatcagtg aactttcgta attaataaat gtagaatact   11820
gctgtaaggc aaattgcgct ttaatcatcg attctgggtt gagcaaatca ttaccattca   11880
ttttgtcatt aatggcctgg cctgcctggt gcgccatgtg ggagagcata tccactaatt   11940
gtgcaatatc cataatgctt ttccttaaaa taaatacatc gtaaggatac tggcaacata   12000
gcaaaattta gaaagcaatg aacatccggt atatacctga aaacgattac tccggcgcac   12060
gttgttctgg cgttacctga gccagcaaac gatataatgg gctgctgacc tgcataccgg   12120
tcattgccat cccatccata ccgaagcgag taaaactcat tagtccatag gtaatatcat   12180
taagacgctc taataaatga ggctgtagtc ccaaactacc actccagtat gaatgcgtca   12240
ttaccgtcgc ggttaaggct aatctaccgc ccagggagac ggctttagca atcgccatac   12300
ttttgcgttg attggcgaaa caattagcaa tataaaaaac ggcattgcct atactgtcgt   12360
gagccatagg caaatgatgt ttatgatggt agataagaca ggcgacatcc gcgatggcaa   12420
tagcaaggcc aatccctgcc agggctacga gcggcgcgcc tccaccactt agcactgtta   12480
atgctattcc agcggaacag cataaaatct gtccgcccaa ataaccgtt tgccaactaa    12540 aaatttcttt tggaaaacac tctatcactc gtttcgcaag tccggccaat aaccgctctt   12600
ttccttgttg aggacctatt ctaccactct ccatattggt ttccggatgt ggcaatgagg   12660
gacatggagg tgattcctca ggcgcgttaa caggacgttg ccctcctacc tgagcatttg   12720
ggctaacagg tttcatggtt ctccccgaga tgtatgacca gaactgtcca ttaatgcagg   12780
tgcagtagca gattgacaga gcgctgccat ttgttccgcc aataacgcac tgggatcggc   12840
ataaagttca tcaacagaat tttcctgatc gtcgccagag gggcgggcaa ggcaataatc   12900
cagtaccgca cctatcgccg tcaggctaac ggaggtaatt acactcccca tgtccaaaga   12960
ggccgcaata ttttcagccg cgggcagtgg aaactgtagg ggtaaaacca acatagaaat   13020
agcgattcct gaacgtatta ataaagaaag acaattagca agggtgttag cgcagttaag   13080
acttgcccca catttttaagg ccagcgcact gaccacaaga gcaacgctat cactggcggt   13140
ttgtaatggc tccttttgct gacatatcga ttgataatta tgatacgcac agcaagcatc   13200
cccaatagca atcacgagcg ccgcccccgc aagaatagca atgggtaatc ctgccccgcc   13260
agaaattacc gctgcagcaa ccgataaccc aaacacgact gtcgcaccca gcgcacgaat   13320
agtgtattgc ataaaatgta tagcataatc cctctgctgc cttatttgtt caggcgtaag   13380
cagcacaggg gctgcggggg taccaggcgc tggaatttca ggggaggaa acgatacctc     13440 cttcgcttgt atatcggaag gaggactatt accatcgact atattacttg ccgctgacgg   13500
aatatgaatt ttcatatttc gttctgttat ttaagcaata agagtatcaa ccattatttg   13560
cgcattctgg cgaatctcac tccatgaggc atccgcataa ctcatcttga ttgcggtttg   13620
aaaagcctct ctcgccaacc cgggttcccc catcattttg agacagacgc ccgtttggta   13680
```

```
aaccggttct ggatggctgg catccagcat caaggcatgt ccatagaaat taatggccgt  13740
tgtgtattct ttaagcatca tccaggtgcc agccaatgca atatgggcac gccaactcca  13800
tggctgggcc atcaccagcc aactaaaatc gattacggcg cgcgaataat ccccctcctg  13860
ccatgaggcg taaccactgg cataaacggt ttccggatca acggataata gctgtttcag  13920
aatgtcttcg ggtattttat ttttctgatc ttctttcatc atcataccta ttgattgtta  13980
ttttcacgtg ataatgattt acgttaggaa ggtcatttaa aaacgtcgct ggataagatg  14040
ctcggcggat aaaactgtcc agttatcgcc atcaagctgt gtaaaggtcg ctcccattac  14100
tgtcaggatg cgcaataatt tcctgcgtag catggctttt ttttcatcca gaacgtcggt  14160
gattatcaac atctttaaac atgttaactg cgggtgatgc acaaatatcc cgcgtaaaag  14220
tcccagtaag tgaaacaatt gctgtggtcg aggttgcccg ggcgtcaggc gcctgaactc  14280
acaaataatc atttcttttg cctcaatacg atagatcacc aggtaaggcg ataatataaa  14340
ctgctgccca gtaatatgg cggtctcccc taaatatgca ggctcagtaa acacctgatg  14400
ccgacgcaac cattgctcta tttcttgcac catgtttacc tcgttaatgc ccggagtatt  14460
tcagcaagaa ccgtgaccag tgacgacccc acgccgatga tttgctgcat aatttcagtt  14520
gctttctccg taatttccgt cagggattta ttataagatt gggcccccatt ttgttgcagg  14580 tcggcaatcg ctttatcttg atcactttga cgttgcgcta caccagcccc caggcccatg  14640
acgcccccag ctgtgtggcc tacggcttga cccgctataa gaccggtttc cccgcctacg  14700 gccctaatc ctatcgtcag tacacccgac aacattgcgc caccegcagt aatcattgat  14760 gctctaaacg cttcatcaat tgtttcatt tgcgtctgta aaacattgac ttgcagttcc  14820
caggccagcc gttgttttc tacgttatag ctgcgcatga tatcgcgcag cttttggca  14880 agctccatta gcttcatcca gatatcatca ataacagaa gcattgattc agtacccatt  14940
ccctccccgg agggagatgg agtggaagaa ggtgttaaca aggaaggcgc tggtaatacc  15000
agtgctacgt tactcgcttc catattttta tcctcagatt aagcgcgata gccagctatt  15060
ctcgcctgaa cgctactata gtgatcaatg gtatctaata catctctaag cgcggcaccg  15120
ctccccttat aaagcttctc taagcgtttt tgttctatct ttttctggtt ttctgtttgt  15180
tgcattatga aatccagaaa ccgttgctga gttattaatt gctctatttt cttttcgatc  15240
ttcgcttttt ctgtgttaac catgccagta ttcatctgac tggcgccctc ggttgcacat  15300
ctgatagcct gtaagccttt aaatgaacaa tccctcagta aggcatacag gatttttttg  15360
aacatattga agagaacttt attacggaat ttttttaaca ggaactttcc accttcttgc  15420
acacattttt ccagggcttc ttttgccgct tcttttgcca tggctttcac cccctctttc  15480
gtaaagcttt ttcccgcgct tcgcgtcata ttattttcta cgttacgaga aaactcggca  15540
gcctcctctg ccatctcatt cgccatagcc atttcacgtt caagcggctc aaattgtttg  15600
gaaaaacttt cgctcacttc ttcgccaaac ttttcagcca actcctctat ttctgcttcc  15660
cctgcaccta ccatacgctc aaccacttcc tcgccaaaac cggagtcaag cacttttgca  15720
gctgcgccag ataaacctct cgtcgccata aaagcacggc caatctggaa acatccagt  15780 gccagcgcga cggcttcaca accaaattga atcttacttg tcacgtcaat aattgcctga  15840
caggtatcgt ggtcagcacc gcacatcatt gccgtttcgg ctccggcttt aaccattcct  15900
gcacaaccta cggctatata agctacgccg ctagccattt ctgcgggatt accggacaga  15960
aacccctcca caacttttaa ggagccaatc acagttcaa atatgccggt aatccagtca  16020
aaaatagcgc caaaaatgcc cgctttacgc gctttatcct cctgctctat cgctttctgg  16080
```

```
atctgctcct gatactcctt tacctgctta tcacgtaatg cattttgcac ctcagttgcc   16140
cgctcaagct gttggcataa cgattgagcg ttattaccaa aaacgctgag tattaatgtc   16200
gtcatcaaca ttgataaaac cgcgggattg gtctgcaaaa agtcaggcaa tgatagacgc   16260
ttatgatttc cgggtacggc atcaagcagt tgcttcaacg cattgcttgc ctcctgaaga   16320
ctaattttcc ctgataacag gcacgcgcg ttgccatcgc caaaagtaga attcacacga    16380
tgccggcgct ttcccagcga acccgaggaa acgcaactga cattgcttaa gtgatgatgt   16440
gttaaggcgg ttactcctgc ggtgctgtcg ctattactgt gaattcgatt cattttagc    16500 tcctgtcaga aagttgctgt aacatctttt ctgcacgctg tcggagaatt tgatgttcac   16560
tgacctcgcc gcaaatacgc accacggcct ttaacgcttt gattgcataa cagacgttat   16620
cacacgcgag atagcattcc gctgcggccc atggcgcctg cggcgcatca atcttaattt   16680
gtgccgcgcg tccataagcg tatatcgctt cccccaatg tttttgagcc tggcagcatt    16740
cccctaacct aaaccagtag tcaaatgacc aggcatcata tatcgtcaac aattgaaaaa   16800
gtcgcgctgc gccggcgaac tcttttacct ccataagctg catggcatag cgatacagag   16860
tattaagcgg ctgtgtaaca tcgtcatcca acaaatacg cagcgagccg ccacgccgga    16920
aaaaccgcat cgtgtcatgt gcctgttgta gggtcgggtc ttttttcatg agtacgtttt   16980
ctgcgctatc atactggaaa ttcccccca cttactgata gccctgtca gttgggtaag     17040 gacagcgtta agctcctgag acattttttg aattgttatc tgcccctgac tcataagatc   17100
ggtattccgg ttggcgtcat tatccaaagc cgctttgatc gcctgtaggc caccttatc    17160 cagcttccca tgatcgccat atttagccat ataatcatca atggtcatac catcgatgag   17220
aataccatta tcacgcatgt atttaattac atcctcaggc acctcctctt tggttttagc   17280
atcccctttg gctgctttag caatcacctc atccatctca tttgactttt cctgggtatt   17340
tctggcacgt tcagcgttct tctggacttc aataaattta ttatttgcga tatcctgaat   17400
aaccataagg agaataagca aaacaccata cccttcggca aacggatttt gctgggataa   17460
gtcatcctgg ctcccggtat cagcgttgct gacgccgaag ctatttttaa acacaatagg   17520
gttttgactt ccccataaga tgtttcctga agacattatg ctttaccttt ttgttttttcc  17580 tgacggtatc tccaccgggg cttgagcatt aagttgtttc agtcgtactt caagttgttt   17640
aaacaaactt actattttct ttaaatcctt ctcggcctcc tggttaaccc cggcaacgcc   17700
ttgtggaaat aggttttgaa gaatactctc tgtctctctg ctcttttttgg ggctctctgc  17760 cctttcagca agctgttgac tcaccttagc ccggatttgg tgaaattttt taagacagtg   17820
atttagctgc atgtaacttt gctctaaatc acgatattca ctaaacgcag ccttttttctt  17880 tatcattatt cccctccata tacacgatag ataattaacg tgctaactaa gagcctatcc   17940
cattagggct atttttacttg ccattttgaa cctgggcagt gctcaaaatc ctcacgtact   18000
acgtgtacgc tccggttttt gcgcgctatc cgtgtccaaa ctggctgcgc caattaacgc   18060
ctggtgggat aggctctaag atattttttac tttactcttg ctcactcact acaagtgcgc  18120
tgttatggta acgataataa ataatgttga tgatattttc ggcctgctcg atcgcttcaa   18180
gcaataaggt gttttgctga tattgctgcg gatcctgtaa cttgccgttg ttctctccta   18240
actgtttccg ggcagccctt aattgtaaaa ttatgccttt ggcctcttca cgcgaatgaa   18300
gcagcaaatc ttctaaccgg gtcaaagttg tcatttttcca ctcacttaaa atctaatgga  18360
tagttaatca aagtatcata atgtttaatc gttaccacat cggcactcag atggacaatt   18420
tctcccccat tgggtaacaa tgcccctaca cgtaaacgct ctttattcgt cagtaataag   18480
```

```
taattaccat ggcgactctg tacaaagcca gccactggcg caggcagata cttgctttca   18540
tcatgggaag gcgcaatatc ctgataaatt aaagaaagag cgggatcctt tttctttaat   18600
gctgctaacg tttcttgcaa aatgcgttga tgagattcat ccagtacacc actgataaca   18660
aaagagcgcc gcattggcgt aacattgaca agccccacta aaccgttctc tattatcgca   18720
gaaataatat catctccctg agactgatga gagtgactaa tctgccagtg caataacccg   18780
ggaatatctg caagtaatgg ttgaacctta cgccattgct gatccatttg tatatcatca   18840
tgaattaaca cgctccccgg cccttcgctg gatacttcag catgcgggta acccattttt   18900
atcaaaacat cctgcacttc tcgtaccaat aagtcatcac agattacacc atcccgatac   18960
atgacccccc atgattcgag agtcgctctc accttttgca tctgttcgct tgacgagcaa   19020
taaccggaca actgcaggct gccatcttct ttccattgcg cccgcacata atgaatattg   19080
cttttgtcta ataaaaactt aacccgcaaa ggtaagtcat ttaccgtttc aggctgacca   19140
ctaatactta acaggacacc cattccaccg atgaaaatca agaatacgcc agccaaccac   19200
cagtaccctg atctggaaac gggtatttga taatcagcaa gttcacaatc ctgtttacca   19260
aacgcgatag ccactcccgc aacctgcaaa accccactgg atggtagcgg cttatttgga   19320
ttaaatctgc ggccattaac tctaactctg gctttcccgg catcaacaaa taaattatct   19380
gcctgttctc tcagaataat ttttcattt atagtaagcg gaatacaaat atcgcatcct   19440
ttctccccca gtgacaggtt accttcattc agccatactt cccggccttg taaaacgtga   19500
cctaaaaaac gtattttcca ggaactcttt ggattaacca tgagatatgc cattatttac   19560
tactgaggct ttaatcaaaa aaagcctgat tacactatgt acttgagtcg tatcattgcg   19620
aaacaaatgg cctacgacag gaatatcgcc caataaagga attttatttt gcgagtggat   19680
ttgtttacct tgtttaaatc ctcccagcaa tagactttgc ccggccaata atgtggcctg   19740
cgaagcaatt tcagaatttt gcacttcggg cagcgggtct gtttcgcttt gcgtatcact   19800
ttgttgtcca tcctgaatat taagatcaag cattattttt tgcgtgccat tatcatttaa   19860
caagcgaggt gtaacgcgca acaaagaacc cgtagtgatg gattcaagtt tagccacttt   19920
ttctccctgc agtttggtat agaaagtaat attttatcc agcacagcct ggatattatt   19980
taaagtcacc acagatggct gggaaagtac ataagcctga gagcttttt ccagggcatt   20040 caaacgcacc ataaagtttg aggtatcgct gattaccgtt gaaaaaccgc tagcaccacc   20100
gtcattcaaa cctgtattga acgcaatttt cttgccaccc agcgacactg ccgttcccca   20160
gtcgatgcct aactggttaa tatctccagc attaacatcg ataattttca ccgaaatctc   20220
tatcatctgc tggcgttgat ctaattctgt gataagtttc cgatacccgg ccatattgga   20280
cgcataatca cgaacgatca ctgcattctg gcgtgggtcg gcagcaaaca tgggcaatgc   20340
ctgtgtagcg ggtgaaccat tgttcgtcga tgacgccggt acgctggttt tactcatctc   20400
acgcaataca ctcacgaccc ctggaaccac gacggactga tcgcgatatt ggtattgggt   20460
atccatcgca gtggcatact taagcgtgta tatacttaca ctcaccgcac tgtcttttcg   20520
tttgattaac gcattatcca gcactgaagc taattgacta atacgagtca ggcagctggg   20580
aacaccgctc acctcacag ctttggtacc ggtaatttct ttaacctcgc atcccggtga   20640
tgaaagaata ttctggctgc gtaagtaatg aatgaaccgt ccagtagata aaatattgaa   20700
agtgataacc tgatgtttta ataacgatgc aggatataca tataacatgc tgccatcaaa   20760
ccaggtaagc aaatcatatt gtgctgccag gttattcaaa atatcgaccg gtggtccagg   20820
cggaattttt ccactaaatg tagctgttat caatgggcta atagtaatag ccgtatcata   20880
```

```
gttctctgag agcagatgta aaacctctgc taatggcatt tgtctggcat aaagggtgaa   20940
gtcattacct ttccatgata actcatcact ctttgctgta ttgagtataa atagtaaaat   21000
taagattaaa cgtttattta ctaccatttt atacccacc cgaataaagt ttatggtgat   21060
tgcgtattac atttttttaaa atgcaagtta aagccaggtg ttttttctatc tcaatagcaa   21120 taagctcaga gctactactt gtggtataat aaccgtttaa ccatccccca tccgctgtga   21180
gctgtatagc ataatcatgg acgtccgggt gtgctgcaag cagtagtgtc acataggcaa   21240
gacaaggctt aggtaagctt tccaggtcat ttaagaacaa agaaatagaa aatgcttctg   21300
agaaaatttc tcctctggca ggatgcccat caatagtcat tatccaggat cggctattac   21360
cttcggcctt gatatcctga attaatggaa tgccttttaa aactgccagc atgaatccct   21420
cctcagacat aaatgggagt ttctatcaaa ttcgctcaca accacatccg taaaaagcct   21480
gattcacatt tatttcgact atacttttct tgtacaatat caggatgctg tctacatata   21540
ccttgtcaca ggcgattcta tcattcggat tttccgataa attcacaatt acattttcag   21600
cactgacata aaaacttaca atttgaaaaa tcatttatta aatgaactgt tacgatgttt   21660
ttacatcgcc atcttattaa aaagtaattg tagtcatcga ctgggttata tatgaagaaa   21720
tttatcttcc taatgataac accatcgatt aatcttctga tgaaactata tgtactgcga   21780
tagtgatcaa gtgccaaaga ttttgcaaca ggcaactgga gggaagcatt atgaatttgc   21840
tcaatctcaa gaatacgctg caaacatctt tagtaatcag gctaactttt ttattttttat   21900 taacaacaat aattatttgg ctgctatctg tgcttaccgc agcttatata tcaatggttc   21960
agaaacggca gcatataata gaggatttat ccgttctatc cgagatgaat attgtactaa   22020
gcaatcaacg gtttgaagaa gctgaacgtg acgctaaaaa tttaatgtat caatgctcat   22080
tagcgactga gattcatcat aacgatattt tccctgaggt gagccggcat ctatctgtcg   22140
gtccttcaaa ttgcacgccg acgctaaacg gagagaagca ccgtctcttt ctgcagtcct   22200
ctgatatcga tgaaaatagc tttcgtcgcg atagttttat tcttaatcat aaaaatgaga   22260
tttcgttatt atctactgat aacccttcag attattcaac tctacagcct ttaacgcgaa   22320
aaagctttcc tttatacccca acccatgccg ggttttactg gagtgaacca gaatacataa   22380
acggcaaagg atggcacgct tccgttgcgg ttgccgatca gcaaggcgta tttttttgggg   22440 tgacggttaa acttcccgat ctcattacta agagccacct gccattagat gatagtattc   22500
gagtatggct ggatcaaaac aaccacttat tgccgttttc atacatcccg caaaaaatac   22560
gtacacagtt agaaaatgta acgctgcatg atggatggca gcaaattccc ggatttctga   22620
tattacgcac aaccttgcat ggccccggat ggagtctggt tacgctgtac ccatacggta   22680
atctacataa tcgcatctta aaaattatcc ttcaacaaat cccctttaca ttaacagcat   22740
tggtgttgat gacgtcggct ttttgctggt tactacatcg ctcactgcc aaaccgttat   22800 ggcattttgt cgatgtcatt aataaaaccg caactgcacc gctgagcaca cgtttaccag   22860
cacaacgact ggatgaatta gatagtattg ccggtgcttt taaccaactg cttgatactc   22920
tacaagtcca atacgacaat ctggaaaaca aagtcgcaga gcgcacccag gcgctaaatg   22980
aagcaaaaaa acgcgctgag cgagctaaca aacgtaaaag cattcatctt acggtaataa   23040
gtcatgagtt acgtactccg atgaatggcg tactcggtgc gattgaatta ttacaaacca   23100
cccctttaaa catagagcag caaggattag ctgataccgc cagaaattgt acactgtctt   23160
tgttagctat tattaataat ctgctggatt tttcatgcat cgagtctggt catttcacat   23220
tacatatgga agaaacagcg ttactgccgt tactggacca ggcaatgcaa accatccagg   23280
```

```
ggccagcgca aagcaaaaaa ctgtcattac gtacttttgt cggtcaacat gtccctctct    23340
attttcatac cgacagtatc cgtttacggc aaattttggt taatttactc gggaatgcgg    23400
taaaatttac cgaaaccgga gggatacgtc tgacggtcaa gcgtcatgag gaacaattaa    23460
tatttctggt tagcgatagc ggtaaaggga ttgaaataca gcagcagtct caaatcttta    23520 ctgctttta tcaagcagac acaaattcgc aaggtacagg aattggactg actattgcgt    23580
caagcctggc taaaatgatg ggcggtaatc tgacactaaa aagtgtcccc ggggttggaa    23640
cctgtgtctc gctagtatta cccttacaag aataccagcc gcctcaacca attaaaggga    23700
cactatcagc gccgttctgc ctgcatcgcc aactggcttg ctggggaata cgcggcgaac    23760 cacccccacca gcaaaatgcg cttctcaacg cagagctttt gtatttcccc ggaaaactct    23820
acgacctggc gcaacagtta atattgtgta caccaaatat accagtaata aataatttgt    23880
tacccccctg gcagttgcag attcttttgg ttgatgatgc cgatattaat cgggatatca    23940
tcggcaaaat gcttgtcagc ctgggacaac acgtcactgt tgccgccagt agtaacgagg    24000
ctctgacttt atcacaacag cagcgattcg atttagtact gattgacatt agaatgccag    24060
aaatagatgg tattgaatgt gtacaattat ggcacgatga gccgaataat ttagatcctg    24120
actgcatgtt tgtggcgcta tccgctagcg tagcgacaga agatattcat cgttgtaaaa    24180
aaaatgggat tcatcattac attaccaaac cagtgacatt ggctaccta gctcgctata    24240 tcagtattgc cgcagaatat caacttttgc gaaatataga gctacaggag caggatccga    24300
gtcgctgctc agcgttactg gcgacagatg atatggtcat taatagcaag attttccaat    24360
cactggacct cttgctggct gatattgaaa atgctgtatc ggctggacaa aaaatcgatc    24420
agttaattca cacattaaaa ggctgtttag gtcaaatagg gcagactgaa ttggtatgct    24480
atgtcataga cattgagaat cgcgtaaaaa tggggaaaat catcgcgctg gaggaactaa    24540
ccgacttacg ccagaaaata cgtatgatct tcaaaaacta caccattact taatattatc    24600
ttaattttcg cgagggcagc aaaatgaaag aatataagat cttattagta gacgatcatg    24660
aaatcatcat taacggcatt atgaatgcct tattaccctg gcctcatttt aaaattgtag    24720
agcatgttaa aaatggtctt gaggtttata atgcctgttg cgcatacgag cctgacatac    24780
ttatccttga tcttagctta cctggcatca atggcctgga tatcattcct caattacatc    24840
agcgttggcc agcaatgaat attctggttt acacagcata ccaacaagag tatatgacca    24900
ttaaaacttt agccgcaggt gctaatggct atgttttaaa aagcagtagt cagcaagttc    24960
tgttagcggc attgcaaaca gtagcagtaa acaagcgtta cattgaccca acgttgaatc    25020
gggaagctat cctggctgaa ttaaacgctg cacgaccaa tcatcaactg cttactttgc    25080
gcgagcgtca ggttcttaaa cttattgacg aggggtatac caatcatggg atcagcgaaa    25140
agctacatat cagtataaaa accgtcgaaa cacaccggat gaatatgatg agaaagctac    25200
aggttcataa agtgacagag ttacttaact gtgcccgaag aatgaggtta atagagtatt    25260
aa                                                                   25262
```

<210> SEQ ID NO 3
<211> LENGTH: 6053
<212> TYPE: DNA
<213> ORGANISM: Artificial Sequence
<220> FEATURE:
<223> OTHER INFORMATION: spvRABCD operon

<400> SEQUENCE: 3

```
atggatttct tgattaataa aaaattaaaa attttcataa cactgatgga aacaggttcc    60
```

```
ttcagtatcg caacatcagt actgtatatc acccgaaccc cgctgagcag ggttatttca    120
gacctggaaa gagagctgaa acaaagactc tttatacgga agaatggcac tcttatccca    180
accgaatttg cacaaactat ttatcgaaaa gtaaaatccc attatatttt cttacatgca    240
ctggagcagg aaatcggacc tacgggtaaa acgaaacaac tagaaataat atttgacgaa    300
atttatccgg aaagtttaaa aaatctgatc atttcagcac tgaccatttc cggccaaaaa    360
acaaatataa tggggagagc cgttaacagc caaataatag aagaactgtg tcagacaaac    420
aactgcattg ttatttctgc cagaaattat tttcatcggg aatcgcttgt ctgccggaca    480
tcagtggagg gtggggtcat gttatttatt cctaaaaaat tctttctctg cggcaaacct    540
gatatcaaca ggctggccgg aacacctgta ctttttcatg aggggctaa  aaattttaat    600 ctggacacca tataccattt ttttaaacag acactaggta ttaccaaccc tgcattcagt    660
tttgataacg tcgatttgtt cagttcactg taccggttac aacaagggct ggcgatgtta    720
ctcatccccg tcagagtctg tcgggctctg ggattatcaa cagatcacgc actgcacatc    780
aaaggcgtag cgctctgtac ctccttgtat tacccgacca agaaacggga gacaccagat    840
tatcgtaaag ctataaaact gatacagcag gaactgaaac agtccacctt ctgacccttat    900 gcagcgtaag ggccgcaaca cctgtattca cggcatttgc cagattcaga ttgtcagcaa    960
tccccatcct ccatagcggt agttcaccgc ggagcatgga gtaaaccggc tggtcgccgt    1020
caatctgaca cagaatcagt ttgatgctct ggtggattac ctaaacatgg gcattaacg    1080 cgctggctca cgccacttta ctgaagaaac tgaataacgg tgactatgac ggcgcagcga    1140
atgaattcct gaaatgggac cacgccagcg gtcaggttgt tccggcctg acccgacgcc    1200 ggagcgctga acgttgttta ttcctgagtt aatttgttgt gccatctttg cacaccggga    1260
accgcgattc cgcacagcag aaaaatagca cataaataaa ctcaatataa gccactcatt    1320
ttctggcaat acaaaataat tcccctgcag acattatcag tcttcaggat ttcattctgt    1380
ttattttcag gagtcatcat tatttatgaa tatgaatcag accaccagtc cggcactttc    1440
acaggtcgaa accgccatcc gggtcccggc agggaatttt gcaaaatata attattattc    1500
cgtgtttgat attgtccgtc agacccgtaa acagtttatt aacgccaata tgtcatggcc    1560
gggatcccgc ggaggtaaag cctgggacct ggcgatgggc caggcgcagt atatccgctg    1620
catgttccga gaaaatcaat tgacccgcag agttcggggg accttgcagc agacaccgga    1680
caatggcacg aacctgagca gttccgctgt cggcggtatt cagggacagg cagagcgtcg    1740
gccggacctg gccaccctga tggtggttaa tgatgccatt aaccagcaaa taccgaccct    1800
gctgccgtat cattttccac acgaccaggt ggagttatct ctgctgaata ccgatgtgtc    1860
gctggaagat attatcagcg agagcagcat tgactggccg tggttcctga gcaactcgct    1920
gaccggcgat aacagtaact atgccatgga gctcgccagc cggctgtcac cagagcagca    1980
gacactgccg accgagccgg acaacagtac cgccactgac ctgacctctt tttaccagac    2040
caatctgggg ctgaaaaccg ccgactatac gccatttgaa gcactgaata cctttgcccg    2100
acagttagcg attaccgttc ccccaggtgg aacagttgat tgcgggtact ctgcgtgcca    2160
gccggcagtt tagcttcccg cgctaccaga gtagtgagca gcagaccatt ctgcagaatc    2220
tgagcgacgt cattgttcag gtgcattcta ccgcgctgta cggcggcagc acttttgaac    2280
aggccgtaga gcagacgctg taagcagaaa atatacctgt ccatcgtcag acggccagtt    2340
tcaggagata gtgtatgttg atactaaatg gttttcatc tgccacttta gcgctgatca    2400
ctcccccttt cctgccaaaa gggggcaagg cgctgagtca gtcaggccct gacggcctag    2460
```

```
ccagtataac gctgtctctg cccatcagcg ccgaacgcgg ctttgcgcct gcgctggcgc    2520
tgcactacag cagcggtggc ggcaatggcc ccttcggcgt gggctggtcc tgcgcgacaa    2580
tgagcattgc ccgccgcacc agccatggcg tgccgcagta taacgacagc gatgagtttc    2640
tggggccgga cggagaagtg ctggttcaaa cgctcagcac cggtgatgcc cccaatcccg    2700
tcacctgctt cgcgtacggt gacgtatcgt tcccgcaaag ctacacgtg acccgctatc     2760 agccccgcac ggagagcagt ttttatcgcc tggagtactg ggtgggcaac agcaacggcg    2820
atgatttctg gttactgcat gacagtaacg gcatcctgca cctgctgggg aaaaccgccg    2880
cagcacgcct cagcgatccg caggccgcct ctcatacggc gcaatggctg gttgaggagt    2940
cggtgacccc tgccggcgag catatctatt actcctactt ggcggagaac ggtgacaatg    3000
tggacctcaa tggggacgag gccggacgcg atcgcagcgc catgcgctat ctcagcaagg    3060
tacagtatgg caacgcgacc cccgccgccg atctgtacct ctggactagc gccacacccg    3120
cggtacagtg gctgttcacc ctagtgtttg actacgcgca acgtggtgta gatccacagg    3180
taccgcctgc attcactgct cagaacagct ggctcgcccg ccaggatccc ttctccctgt    3240
ataactacgc ctttgagatc cgcctccatc gcctgtgccg ccaagtcctg atgttccacc    3300
actttcctga tgaactgggt gaagccgata cgctggtttc ccgtctgctg ctggagtatg    3360
acgaaaatcc gatactgaca cagctttgcg ctgctcggac gctggcctat gaaggcgacg    3420
gttatagaag agctcctgtc aacaatatga tgccaccgcc accgccaccg cctcctccga    3480
tgatgggagg taattcatct cgaccaaaat caaaatgggc gattgtagag aatcaaagc    3540 agattcaagc tctgaggtac tattcagctc aagggtacag tgtgattaat aaatatttac    3600
gtggggatga ttatcctgaa acacaggcaa agaaactct gctctccaga gactatcttt    3660
ccacaaatga acccagtgat gaggagttta aaaatgccat gtcagtttat ataaatgata    3720
ttgtggaggg attaagttca cttcccgaaa cagatcacag agtcgtatac cggggcctga    3780
agcttgataa gcccgcatta tcggatgtgc tgaaggaata cactactata ggtaatataa    3840
taatagataa agcttttatg agtacatcgc cagataaggc atggataaat gacactattc    3900
tcaacatata cctagaaaaa ggacataaag gtagaatact cggagatgtt gcacatttta    3960
agggagaggc agagatgctt ttccctccaa atactaaact caaaatcgaa agcattgtaa    4020
attgtggatc ccaagacttt gcaagccagc ttagtaagct gagattaagt gatgatgcaa    4080
ctgctgacac aaacaggata aaagaataa taaacatgag ggtactcaac tcatagatac     4140
taagaatcta ttccagaagt ggtatgagcg gcctagctct ataagggtt atactccgga     4200 accccagatt tttccgtcac cctaggcccg caaagtagtg catctaaact tttgccatta    4260
cccttcttta actttctgct cggaacggac cgaaatatca ttttttcgcc tgataaaaaa    4320
tgaggttttc tggataacta atcgttttat taaaaaaaac tgagaattta tatctaataa    4380 tatgcgata tatccatatc gcaaaggaga tttcccatgc ccataaatag gcctaatcta     4440
aatctaaaca tccctccttt gaatattgta gctgcttatg atgggcgga aataccatct     4500 acaagtaagc acctgaaaaa taatttcaac tccttgcaca accaaatgcg gaagatgccg    4560
gtatcccact ttaaagaggc gctggatgtg cctgactatt cagggatgcg ccagagtggt    4620
ttctttgcta tgagccaagg ttttcagctg ataaccatg gttacgatgt tttcatccat    4680
gctcgtcgag aatcacctca gtctcagggc aaatttgccg gtgacaagtt ccacatcagt    4740
gtgctcaggg atatggtgcc acaagcattt caagcgctgt ccggattgct gttttcagag    4800
gacagtccgg tagataagtg gaaagtgacc gatatggaga aggtcgctca acaagaccgt    4860
```

```
gttagcctgg gcgctcagtt cacgttgtat ataaaaccag accaggaaaa ttcgcagtac    4920
agtgcgtcgt ttctccacaa gacacggcaa tttatagagt gtctggaatc cagactatcc    4980
gaaaatgggg ttatttcagg acagtgtcct gagtcagacg ttcatcctga aaattggaaa    5040
tatctcagtt atcgtaatga actacgaagt gggcgtgatg gtggcgaaat gcagagacag    5100
gctttacgtg aggaaccgtt ttatcgtttg atgacagagt aagtatgggt ttggggagca    5160
acggaacagt aaacgccgtt aaacaactat tttaaatgct cattaattta ttaatcaata    5220
aattacaaat tttcattgaa ggctcccccc ttactgacga attccggcac cgtaaaggaa    5280
taacgctcat gcatattgat gtgtccgcac tgtaatggtg aaaattacat aagcaagagc    5340
gttttttgaa aaatattata tttaatgttt tgtaatatgc atttttattga ggtagtgtaa    5400 ctatgagagt ttctggtagt gcgtcatccc aagatataat atcacgtata aattcaaaaa    5460
atatcaataa taatgattca aatgaagtca agagaattaa agatgcgctt tgtattgaat    5520 caaagagag aattttgtat ccaaaaaatt tgagtctaga taatttaaaa caaatggcta    5580
gatatgtaaa aatacatac atccattact ctgggaactg cgttttatta tcagcgtgtt    5640
tacattataa catacatcac cgacaggata tattaagttc gaagaacact gcctctccta    5700
cagtgggatt agacagcgcc attgttgata aaatcatttt tggtcatgag cttaaccaat    5760
catattgttt aaattccatc gatgaggtgg aaaaagaaat attaaccgt tatgacatta    5820 agagggaaag ttcttttatc attagcgcag agaactacat agctccaata attggcgaat    5880
gtagacatga tttcaacgct gtggttatct gtgaatatga taaaaaacca tatgtacaat    5940
tcattgattc ttggaaaaca tccaacatac ttcctagctt acaagaaata aaaaaacact    6000
tctcatcatc aggggaattt tatgtcaggg cttatgatga aaaacacgat tga           6053

<210> SEQ ID NO 4
<211> LENGTH: 1590
<212> TYPE: DNA
<213> ORGANISM: Artificial Sequence
<220> FEATURE:
<223> OTHER INFORMATION: faeHIoperon

<400> SEQUENCE: 4
atgaaaataa cgcatcatta taaatctatt atttccgccc tggccgcgct ggccctgttt     60
tattccgcag caccccgggg ccgaattctt gacggcgggg aaatacagtt tcaccgtctg    120
gtcactgacg aggctccgaa atggacctgg caggtgggct cccctgacca gacatgggcg    180
gtggataccg ctgatgcccg tacagcgaac ggacaactgg ttttgattt acgcggcaag    240 ggctccctgc cgtttctgga aggccatctg tatgaggtgg cagagcgcgg tggtcccggc    300 ttcaccccctt ttatctcctc cagcagtaac gggcagccgt tttccgtgac ggatggcggc    360
acgacgacgg cgcaacactt ccgcgcctct gtcccggtac gtaacccgga aacggtcac    420 gtggcgggac agctttctttt cacccttgac cagggaatgg ccgtcagcgc cggacaccag    480
gaagacgggg cggttctacc ggcagcgatg tcgctcgtaa acgggcagag cgtgacgggt    540
gtgcaggccg gcaccctgcc gcagtggctc aaaaaccgtc tgccttccct gctgatgctg    600 aaccgggggct tcggtaacgg aatgagcacg cagataacg gtcaggttat cagtcagggc    660
gtgctggctg acgccgggt gacccggctg gcggcggcct atgcgtccgc cgtctcggat    720
tttgagctga cgctgccggc agaaaacacg ccggtgcagt ggcaggccgg gctgagtgtg    780
acggtgacgg tccagtaaag aacgggcagg gagaggaaga acacaatgaa acgaatgacg    840 atttactgc tggccgccag tctgctgccg tcctgtgtgc tggcgtggaa cacgccgggg    900
```

-continued

```
gaagacttca gcggagagct gaagctgggc gggccggtga ccagcacccg taatccctgg    960
gtctggaagg tcggggaagg gaacacacag ataaacacga aagctgtctc tgtcctgcgc   1020
agtggggagg aggtaatacc ggttcccctg ccggccatga cggtcctgct gggaaaaact   1080
atcctgacca cccgggccgg ccgggagggg cttgcgccgc aggtgacgta cggtaaggac   1140
acagagggtt ttgcactgac gtggacggca ccgggtatgg catcggtgac actgccggtg   1200 acggggagg gaaatgtccg taccgggaca ttcaccttcc ggatgcaggc ggcgggtgtg   1260
ctgcgccatg tcctggggaa ccgggcgag tatgccgggc tgtatggcga cctgcagggc   1320
aacggcttgc cgccacagac gcaggtgatg ccggcagggc agacgccggg tgtgctgcag   1380
accctgtttg acagtgaagg cccggtctgg ctccgggaga tgacggtcag cagcgtgtcc   1440
ggactgagcc ggttcagtga cgccgccctg cgccaggttg acggggtata cggcgcacag   1500
acggtggcgg acagcggtga gctgcgtttt aaggggggcgg taccgtcccg ctggcatacc   1560
tccctggcgg tgagcattga atatcggtaa                                    1590

<210> SEQ ID NO 5
<211> LENGTH: 70
<212> TYPE: DNA
<213> ORGANISM: Artificial Sequence
<220> FEATURE:
<223> OTHER INFORMATION: SPI-1-P1 primer

<400> SEQUENCE: 5
ttatggcgct ggaaggattt cctctggcag gcaaccttat aatttcatta gtgtaggctg    60
gagctgcttc                                                           70

<210> SEQ ID NO 6
<211> LENGTH: 70
<212> TYPE: DNA
<213> ORGANISM: Artificial Sequence
<220> FEATURE:
<223> OTHER INFORMATION: SPI-1-P2 primer

<400> SEQUENCE: 6
atgcaaaata tggtcttaat tatatcatga tgagttcagc caacggtgat catatgaata    60
tcctccttag                                                           70

<210> SEQ ID NO 7
<211> LENGTH: 21
<212> TYPE: DNA
<213> ORGANISM: Artificial Sequence
<220> FEATURE:
<223> OTHER INFORMATION: SPI-1-P3 primer

<400> SEQUENCE: 7
atgttcttaa caacgttact g                                              21

<210> SEQ ID NO 8
<211> LENGTH: 21
<212> TYPE: DNA
<213> ORGANISM: Artificial Sequence
<220> FEATURE:
<223> OTHER INFORMATION: SPI-1-P4 primer

<400> SEQUENCE: 8
aggtagtacg ttactgacca c                                              21

<210> SEQ ID NO 9
<211> LENGTH: 70
```

```
<212> TYPE: DNA
<213> ORGANISM: Artificial Sequence
<220> FEATURE:
<223> OTHER INFORMATION: SPI-2-P1 primer

<400> SEQUENCE: 9
accctcttaa ccttcgcagt ggcctgaaga agcataccaa aagcatttat gtgtaggctg      60
gagctgcttc                                                             70

<210> SEQ ID NO 10
<211> LENGTH: 70
<212> TYPE: DNA
<213> ORGANISM: Artificial Sequence
<220> FEATURE:
<223> OTHER INFORMATION: SPI-2-P2 primer

<400> SEQUENCE: 10
actgcgtggc gtaaggctca tcaaaatatg accaatgctt aataccatcg catatgaata      60
tcctccttag                                                             70

<210> SEQ ID NO 11
<211> LENGTH: 21
<212> TYPE: DNA
<213> ORGANISM: Artificial Sequence
<220> FEATURE:
<223> OTHER INFORMATION: SPI-2-P3 primer

<400> SEQUENCE: 11
tgttcgtact gccgatgtcg c                                                21

<210> SEQ ID NO 12
<211> LENGTH: 21
<212> TYPE: DNA
<213> ORGANISM: Artificial Sequence
<220> FEATURE:
<223> OTHER INFORMATION: SPI-2-P4 primer

<400> SEQUENCE: 12
agtacgacga ctgacgccaa t                                                21

<210> SEQ ID NO 13
<211> LENGTH: 70
<212> TYPE: DNA
<213> ORGANISM: Artificial Sequence
<220> FEATURE:
<223> OTHER INFORMATION: spv-P1 primer

<400> SEQUENCE: 13
gtgcaaaaac aggtcaccgc catcctgttt ttgcacatca aaacattttt gtgtaggctg      60
gagctgcttc                                                             70

<210> SEQ ID NO 14
<211> LENGTH: 70
<212> TYPE: DNA
<213> ORGANISM: Artificial Sequence
<220> FEATURE:
<223> OTHER INFORMATION: spv-P2 primer

<400> SEQUENCE: 14
ttaccccaac agcttgccgt gtttgcgctt gaacataggg atgcgggctt catatgaata      60
tcctccttag                                                             70

<210> SEQ ID NO 15
<211> LENGTH: 21
```

```
<212> TYPE: DNA
<213> ORGANISM: Artificial Sequence
<220> FEATURE:
<223> OTHER INFORMATION: spv-P3 primer

<400> SEQUENCE: 15
gaccatatct gcctgcctca g                                              21

<210> SEQ ID NO 16
<211> LENGTH: 21
<212> TYPE: DNA
<213> ORGANISM: Artificial Sequence
<220> FEATURE:
<223> OTHER INFORMATION: spv-P4 primer

<400> SEQUENCE: 16
cagagcccgt tctctaccga c                                              21

<210> SEQ ID NO 17
<211> LENGTH: 70
<212> TYPE: DNA
<213> ORGANISM: Artificial Sequence
<220> FEATURE:
<223> OTHER INFORMATION: fae-P1 primer

<400> SEQUENCE: 17
ttaccgatat tcaatgctca ccgccaggga ggtatgccag cgggacggta gtgtaggctg    60
gagctgcttc                                                           70

<210> SEQ ID NO 18
<211> LENGTH: 70
<212> TYPE: DNA
<213> ORGANISM: Artificial Sequence
<220> FEATURE:
<223> OTHER INFORMATION: fae-P2 primer

<400> SEQUENCE: 18
atgaaaataa cgcatcatta taaatctatt atttccgccc tggccgcgct catatgaata    60
tcctccttag                                                           70

<210> SEQ ID NO 19
<211> LENGTH: 21
<212> TYPE: DNA
<213> ORGANISM: Artificial Sequence
<220> FEATURE:
<223> OTHER INFORMATION: fae-P3 primer

<400> SEQUENCE: 19
caggctcccc tgccaccggc t                                              21

<210> SEQ ID NO 20
<211> LENGTH: 21
<212> TYPE: DNA
<213> ORGANISM: Artificial Sequence
<220> FEATURE:
<223> OTHER INFORMATION: fae-P4 primer

<400> SEQUENCE: 20
caggccaact atctttccct a                                              21

<210> SEQ ID NO 21
<211> LENGTH: 22
<212> TYPE: DNA
<213> ORGANISM: Artificial Sequence
<220> FEATURE:
<223> OTHER INFORMATION: spv-S1 primer
```

-continued

```
<400> SEQUENCE: 21
ggtcaattaa atccactcag aa                                            22

<210> SEQ ID NO 22
<211> LENGTH: 20
<212> TYPE: DNA
<213> ORGANISM: Artificial Sequence
<220> FEATURE:
<223> OTHER INFORMATION: spv-S2 primer

<400> SEQUENCE: 22
acgggagaca ccagattatc                                               20

<210> SEQ ID NO 23
<211> LENGTH: 20
<212> TYPE: DNA
<213> ORGANISM: Artificial Sequence
<220> FEATURE:
<223> OTHER INFORMATION: spv-S3 primer

<400> SEQUENCE: 23
ttcagtaaag tggcgtgagc                                               20

<210> SEQ ID NO 24
<211> LENGTH: 20
<212> TYPE: DNA
<213> ORGANISM: Artificial Sequence
<220> FEATURE:
<223> OTHER INFORMATION: spv-S4 primer

<400> SEQUENCE: 24
ccaggtggag ttatctctgc                                               20

<210> SEQ ID NO 25
<211> LENGTH: 20
<212> TYPE: DNA
<213> ORGANISM: Artificial Sequence
<220> FEATURE:
<223> OTHER INFORMATION: spv-S5 primer

<400> SEQUENCE: 25
actgtcgggc aaaggtattc                                               20

<210> SEQ ID NO 26
<211> LENGTH: 21
<212> TYPE: DNA
<213> ORGANISM: Artificial Sequence
<220> FEATURE:
<223> OTHER INFORMATION: spv-S6 primer

<400> SEQUENCE: 26
tttctggtta ctgcatgaca g                                             21

<210> SEQ ID NO 27
<211> LENGTH: 19
<212> TYPE: DNA
<213> ORGANISM: Artificial Sequence
<220> FEATURE:
<223> OTHER INFORMATION: spv-S7 primer

<400> SEQUENCE: 27
tccagaggta cagatcggc                                                19

<210> SEQ ID NO 28
<211> LENGTH: 21
```

```
<212> TYPE: DNA
<213> ORGANISM: Artificial Sequence
<220> FEATURE:
<223> OTHER INFORMATION: spv-S8 primer

<400> SEQUENCE: 28
gaaggaatac actactatag g                                            21

<210> SEQ ID NO 29
<211> LENGTH: 20
<212> TYPE: DNA
<213> ORGANISM: Artificial Sequence
<220> FEATURE:
<223> OTHER INFORMATION: spv-S9 primer

<400> SEQUENCE: 29
gtgtcagcag ttgcatcatc                                              20

<210> SEQ ID NO 30
<211> LENGTH: 20
<212> TYPE: DNA
<213> ORGANISM: Artificial Sequence
<220> FEATURE:
<223> OTHER INFORMATION: spv-S10 primer

<400> SEQUENCE: 30
agtgaccgat atggagaagg                                              20

<210> SEQ ID NO 31
<211> LENGTH: 20
<212> TYPE: DNA
<213> ORGANISM: Artificial Sequence
<220> FEATURE:
<223> OTHER INFORMATION: spv-S11 primer

<400> SEQUENCE: 31
aagcctgtct ctgcatttcg                                              20

<210> SEQ ID NO 32
<211> LENGTH: 21
<212> TYPE: DNA
<213> ORGANISM: Artificial Sequence
<220> FEATURE:
<223> OTHER INFORMATION: spv-S12 primer

<400> SEQUENCE: 32
aaccgttatg acattaagag g                                            21

<210> SEQ ID NO 33
<211> LENGTH: 21
<212> TYPE: DNA
<213> ORGANISM: Artificial Sequence
<220> FEATURE:
<223> OTHER INFORMATION: spv-S13 primer

<400> SEQUENCE: 33
taaggctctc tattaactta c                                            21

<210> SEQ ID NO 34
<211> LENGTH: 19
<212> TYPE: DNA
<213> ORGANISM: Artificial Sequence
<220> FEATURE:
<223> OTHER INFORMATION: spv-S14 primer

<400> SEQUENCE: 34
aaccgcttct ggctgtagc                                               19
```

-continued

```
<210> SEQ ID NO 35
<211> LENGTH: 22
<212> TYPE: DNA
<213> ORGANISM: Artificial Sequence
<220> FEATURE:
<223> OTHER INFORMATION: spv-S15 primer

<400> SEQUENCE: 35
ccgtaacaat gacattatcc tc                                              22
```